(12) United States Patent
Fujiwhara et al.

(10) Patent No.: US 6,239,324 B1
(45) Date of Patent: May 29, 2001

(54) DIENE COMPOUND AND PROCESS FOR PRODUCING THE SAME

(75) Inventors: Mitsuhiko Fujiwhara; Takenobu Nishikawa; Yoji Hori; Toshimitsu Hagiwara; Hisao Iwai; Takashi Miura, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/383,920

(22) Filed: Aug. 26, 1999

(30) Foreign Application Priority Data

Aug. 26, 1998 (JP) .................................. 10-240413
Nov. 12, 1998 (JP) .................................. 10-321700
Feb. 3, 1999 (JP) .................................. 11-025781
Jul. 8, 1999 (JP) .................................. 11-194185

(51) Int. Cl.[7] .............................. C07C 2/02; C07C 2/40; C07C 2/72; C07C 5/41; C07C 15/46
(52) U.S. Cl. .................. 585/422; 585/429; 585/434; 585/438; 560/243; 560/244; 568/450
(58) Field of Search .................... 556/136; 502/152; 514/1; 560/1, 243, 244; 568/1, 450; 585/422, 429, 434, 438

(56) References Cited

U.S. PATENT DOCUMENTS 4,692,548 * 9/1987 Drent ..................................... 560/202
5,113,033 * 5/1992 Myers et al. ........................ 585/506

* cited by examiner

*Primary Examiner*—Johann Richter
*Assistant Examiner*—Brian J. Davis
(74) *Attorney, Agent, or Firm*—Sughrue, Mion, Zinn, Macpeak & Seas, PLLC

(57) ABSTRACT

The invention provides a chain diene compound with desirable regioselectivity, in the presence of a specific ruthenium compound. This chain diene compound is a promising raw material for terpene. It has a structure represented by the general formula (IX):

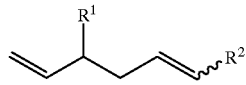

(IX)

wherein $R^1$ represents H, a $C_1$–$C_6$ alkyl group which may be substituted or a $C_2$–$C_6$ alkenyl group which may be substituted, $R^2$ represents a phenyl group which may have a $C_1$–$C_4$ alkyl group or a $C_1$–$C_{12}$ acyloxy group which may have a phenyl group or a naphthyl group, or a benzyl group or $R^2$ is a hydroxy group which reversibly forms an aldehyde group through shifting of the position of the double bond adjacent to said hydroxy group. The chain diene compound is produced by reacting 2-substituted-1,3-butadienes with terminal olefins in the presence of a ruthenium compound in a hydrophilic solvent. Further, the above method provides an inexpensive process for preparing a mild fragrant component and a perfume composition, such as 4-methyl-5-hexen-1-al and 4-vinyl-8-methyl-7-nonenal.

14 Claims, No Drawings

DIENE COMPOUND AND PROCESS FOR PRODUCING THE SAME

BACKGROUND OF THE INVENTION

1. Field of the Invention

The present invention relates to diene compounds, in particular, co-dimer diene compounds. These compounds are prepared through the reactions of conjugated diene compounds with vinyl esters in the presence of a ruthenium salt. The invention especially relates to a chain co-dimer diene compound which is a promising raw material for preparing terpenes. Chain co-dimer diene compounds are obtained by reacting a 2-substituted-1,3-butadiene (a conjugated diene part) with a compound having a double bond at its terminal (a vinyl ester part). The invention also relates to a method of producing these co-dimer diene compounds.

Typical conjugated dienes used in the invention include isoprene and myrcene. The isoprene is reacted with a vinyl ester to prepare 4-methyl-5-hexen-1-al, which is a useful perfume material and can be used in a perfume composition. The invention relates also to this aspect.

Likewise, myrcene gives rise to 4-vinyl-8-methyl-7-nonenal which is also a useful perfume material. The invention relates therefore to 4-vinyl-8-methyl-7-nonenal, a method of production thereof and a perfume composition prepared therefrom. The 4-vinyl-8-methyl-7-nonenal has a strong, aliphatic aldehyde-like fragrance, emanating a citrus—as well as rose-like scent, and can be used as perfumes or in perfume compositions.

2. Description of Related Art

Generally, a small difference in chemical structures among compounds gives rise to a considerable difference in fragrances of the compounds and the other related properties, e.g. retentivity and volatility. The search for new perfumes involves therefore an important workload in such fields as synthesis of various compounds and tests of their fragrance. Among these compounds, aliphatic aldehydes are known as a useful source for perfume essence materials. From this viewpoint, many aldehydes have been produced and put to actual use (Motoichi INDO, "Synthetic Perfume", *Chemistry and Product Information,* 1996, published by Kagaku Kogyo Nippoh). For instance, melonal, citral and citronellal emanate a green melon-like, lemon-like and hawthorn-like fragrance, respectively, and give a specific scent to perfume compositions. They are therefore widely used as a blending essence for a perfume.

As for 4-methyl-5-hexen-1-al, a method of its production from citronellal is reported in *J. Org. Chem.,* Vol. 42, pp. 3622, 1977. This method has the disadvantage of involving many steps and incurring high production costs. Moreover, there has been no description on the fragrant characteristics of 4-methyl-5-hexen-1-al, nor on its use as perfume compositions. Cis-3-hexenal, a compound similar to 4-methyl-5-hexen-1-al, is very expensive, and trans-2-hexenal, another similar compound, has a strongly irritant odor.

In order to form a carbon-carbon bond with butadiene or substituted butadienes efficiently, methods involving a Diels-Alder reaction (B. M. Trost et al., *Angew. Chem. Int. Ed. Engl.,* Vol. 34, pp. 259 (1995)) and reactions with a triple bond (T. Mitsudo et al., *J. Org. Chem.,* Vol. 50, pp. 565 (1985)) have been well-known.

All these methods, however, have the disadvantages that the conjugated double bond of butadienes or its counter part compound must be activated and the regioselectivity cannot be controlled.

Moreover, these methods are susceptible to forming ring products, which is a handicap for the synthesis of chain terpene.

Meanwhile, organometallic reagents have been widely used in reactions for synthesizing carbon-carbon bonds, so as to form desirable skeletons selectively (Japanese Patent Application Laid-Open (JP-A) No. H3-148228). However, these reactions not only involve use of a cumbersome organometal in a stoichiometric amount but also requires the so-called "elimination group", namely, a functional group which does not participate in the structure of the resultant product. This is a disadvantage from the industrial and environmental points of view, and the reactions become costlier. It is therefore desirable to develop a novel route for synthesizing a carbon-carbon bond. This novel route should involve the reaction which does not require any elimination group, and may proceed on a catalytic basis.

SUMMARY OF THE INVENTION

An object of the present invention is to provide a compound having a mild fragrance without emanating irritant odor. Another object of the invention is to provide a method of preparing such a compound, the method involving reduced process steps. The compound can thus be produced at lower costs. A further object of the invention is to provide a perfume composition comprising such a compound.

In view of the above, there has been conceived a novel method of forming a carbon-carbon bond in a regioselective manner through a catalytic reaction. This method allows preparing new diene compounds which provide promising raw materials for the production of terpene.

After extensive studies, the present inventors found that a novel co-dimer diene compound having a desirable regioselectivity can be obtained by reacting 2-substituted-1,3-butadienes with an olefin compound having a double bond at its terminal position (hereinafter referred to as "terminal olefins") in a hydrophilic solvent, in the presence of a ruthenium catalyst, and thus completed the present invention.

A first aspect of the invention concerns a process for producing diene compounds from 2-substituted-1,3-butadienes and terminal olefins. This object required the discovery of a novel carbon-carbon bond-creating reaction which proceeds on a catalytic basis. The process provides a novel compound useful as a perfume component.

A second aspect of the invention relates to a diene compound represented by the following general formula (IX):

wherein $R^1$ represents a hydrogen atom, a $C_1$–$C_6$ alkyl group which may have a substituent or a $C_2$–$C_6$ an alkenyl group which may have a substituent and $R^2$ represents a phenyl group which may have a $C_1$–$C_4$ lower alkyl group or a $C_1$–$C_{12}$ acyloxy group which may have a phenyl group, a naphthyl group or a benzyl group or $R^2$ is a hydroxy group which reversibly forms an aldehyde group through shifting of the position of the double bond adjacent said hydroxy group.

A third aspect of the invention is concerned with 4-methyl-5-hexen-1-al represented by the formula (X):

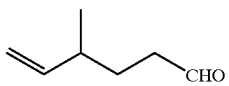
(X)

This product can be obtained easily at low costs by hydrolyzing a compound represented by the formula (IX):

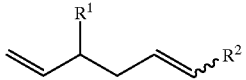
(IX)

in which $R^1$ is a methyl group, and $R^2$ represents a $C_1$–$C_{12}$ acyloxy group which may have a phenyl group, a naphthyl group or a benzyl group or $R^2$ is a hydroxy group which reversibly forms an aldehyde group through shifting of the position of the double bond adjacent said hydroxy group; the wavy line shows cis-isomer, trans-isomer, or a mixture thereof.

4-Methyl-5-hexen-1-al has a high level of fragrance which is easily diffusible, and contains a strongly fresh and green fruit-like scent. This aldehyde compound is milder, less irritating and more fruity in comparison with similar perfume compounds such as cis-3-hexenal and trans-2-hexenal.

A fourth aspect of the invention relates to 4-vinyl-8-methyl-7-nonenal (XI) and a method of preparing this compound from myrcene (VIII), one type of 2-substituted-1,3-butadienes. 4-Vinyl-8-methyl-7-nonenal (XI) gives a strong, aliphatic aldehyde-like fragrance, emanating a citrus—as well as rose-like scent, and thus provides a useful perfume essence material. The product (XI) is also suitable for use as a perfume composition.

To the above-mentioned end, there is first provided a process for producing a diene compound at least comprising the step of reacting 2-substituted-1,3-butadienes represented by the following general formula (I):

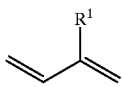
(I)

wherein $R^1$ represents a hydrogen atom, a $C_1$–$C_6$ alkyl group which may have a substituent or a $C_2$–$C_6$ alkenyl group which may have a substituent;
with terminal olefins represented by the following general formula (II):

(II)

wherein $R^2$ represents a phenyl group which may have a $C_1$–$C_4$ lower alkyl group, or a $C_1$–$C_{12}$ acyloxy group which may have a phenyl group, a naphthyl group or a benzyl group; in a hydrophilic solvent in the presence of a ruthenium compound.

Preferably, $R^2$ in the formula (II) is a $C_1$–$C_{12}$ acyloxy group which may have a phenyl group, a naphthyl group or a benzyl group.

In the above process, the ruthenium compound may comprise a ruthenium catalyst represented by the following general formula (III):

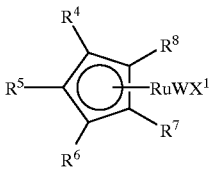
(III)

wherein $R^4$, $R^5$, $R^6$, $R^7$ and $R^8$, which may be the same or different, respectively represent a hydrogen atom or a $C_1$–$C_4$ lower alkyl group, though two adjacent groups among $R^4$, $R^5$, $R^6$, $R^7$ and $R^8$ may be bonded to each other so as to form a five- or six-membered ring; W represents 1,3-butadiene, isoprene, myrcene, 1,5-cyclooctadiene, norbornadiene, 2,3-dimethyl-1,3-butadiene or a halogen atom; and $X^1$ represents a halogen atom.

Alternatively, the ruthenium compound may comprise a ruthenium catalyst formed by mixing a ruthenium compound represented by the following general formula (IV):

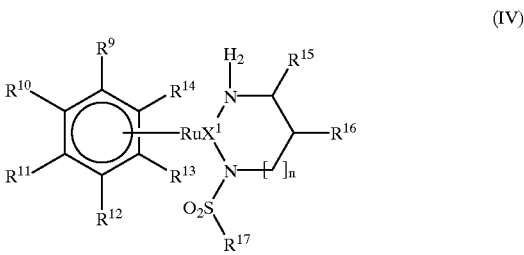
(IV)

wherein $R^9$, $R^{10}$, $R^{11}$, $R^{12}$, $R^{13}$ and $R^{14}$, which may be the same or different, respectively represent a hydrogen atom or a $C_1$–$C_4$ lower alkyl group, though two adjacent groups among $R^9$, $R^{10}$, $R^{11}$, $R^{12}$, $R^{13}$ and $R^{14}$ may bond to each other so as to form a five- or six-membered ring; $X^1$ represents a halogen atom; $R^{15}$ and $R^{16}$ respectively represent a hydrogen atom, a $C_1$–$C_4$ lower alkyl group, a $C_5$–$C_7$ cycloalkyl group, or a phenyl, naphthyl or benzyl group, each of which may be substituted with a $C_1$–$C_4$ lower alkyl group or with a halogen atom, or $R^{15}$ and $R^{16}$ are combined with each other to form a $C_3$–$C_6$ alkylene group; $R^{17}$ represents a hydrogen atom, a $C_1$–$C_4$ lower alkyl group, a $C_5$–$C_7$ cycloalkyl group, a lower alkyl halide, or a phenyl, naphthyl or benzyl group, each of which may be substituted with a $C_1$–$C_4$ lower alkyl group or with a halogen atom; and n denotes 0 or 1; with salts represented by the following general formula (V):

$M(X^2)_a$ (V)

wherein M represents a mono-, di-, or tri-cation such as an alkaline metal, an alkaline earth metal, ammonium, silver, aluminum, lanthanum or samarium; $X^2$ represents an anion such as $ClO_4^-$, $BF_4^-$, $PF_6^-$, $BPh_4^-$ (where Ph represents a phenyl group), $CF_3SO_2O^-$, $CH_3SO_2O^-$, $C_6H_5SO_2O^-$, 4-$CH_3C_6H_4SO_2O^-$, 4$ClC_6H_4SO_2O^-$ or $C_4F_9SO_2O^-$; a denotes 1 when M is a mono-cation, 2 when M is a di-cation or 3 when M is a tri-cation.

Alternatively, the ruthenium compound may comprise a ruthenium catalyst formed by mixing a ruthenium compound represented by the following general formula (VI):

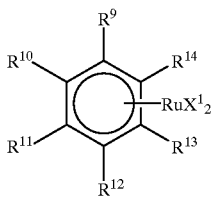

(VI)

wherein $R^9$, $R^{10}$, $R^{11}$, $R^{12}$, $R^{13}$, $R^{14}$ and $X^1$ are the same as defined above;
with salts represented by the following general formula (V):

$$M(X^2)_a \quad (V)$$

wherein M, $X^2$ and a are the same as defined above.

Preferably, a nitrogen bidentate ligand represented by the following general formula (VII):

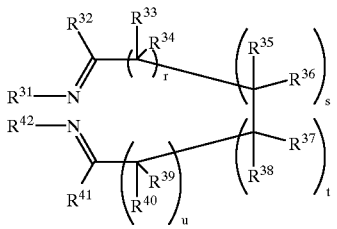

(VII)

wherein $R^{31}$ and $R^{42}$, which may be the same or different, respectively represent an aryl group which may have a $C_1$–$C_4$ lower alkyl group, a $C_1$–$C_4$ lower alkyl group, an aralkyl group or a $C_2$–$C_4$ lower alkenyl group; $R^{32}$ and $R^{41}$, which may be the same or different, respectively represent an aryl group which may have a $C_1$–$C_4$ lower alkyl group, a $C_1$–$C_4$ lower alkyloxy group which may have a substituent or a hydrogen atom; $R^{31}$ and $R^{32}$ or $R^{41}$ and $R^{42}$ may form a ring which may include an oxygen atom; r, s, t and u respectively denote 0 or 1; and $R^{33}$ to $R^{40}$, which may be the same or different, respectively represent a hydrogen atom, a $C_1$–$C_4$ lower alkyl group or a $C_2$–$C_4$ lower alkenyl group, though any two groups among $R^{33}$ to $R^{40}$ may be bonded to each other so as to form a five-or six-membered ring which may have substituents;
is added to the ruthenium catalyst formed by mixing a ruthenium compound represented by the following general formula (VI):

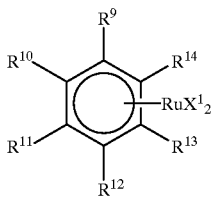

(VI)

wherein $R^9$, $R^{10}$, $R^{11}$, $R^{12}$, $R^{13}$, $R^{14}$ and $X^1$ are the same as defined above;

with salts represented by the following general formula (V):

$$M(X^2)_a \quad (V)$$

wherein M, $X^2$ and a are the same as defined above;
so that the activity of said ruthenium catalyst can be controlled.

In the above process, the hydrophilic solvent may comprise at least one solvent selected from the group consisting of methanol, ethanol, water, or mixtures thereof.

Preferably, in the above process, 2-substituted-1,3-butadienes are at least one compound selected from the group consisting of a) isoprene
b) butadiene; and
c) myrcene represented by the formula (VIII):

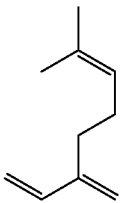

(VIII)

Further, there is provided a diene compound obtainable by the process at least comprising the step of reacting 2-substituted-1,3-butadienes represented by the following general formula (I):

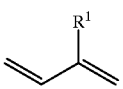

(I)

wherein $R^1$ represents a hydrogen atom, a $C_1$–$C_6$ alkyl group which may have a substituent or a $C_2$–$C_6$ alkenyl group which may have a substituent;

with terminal olefins represented by the following general formula (II):

(II)

wherein $R^2$ represents a phenyl group which may have a $C_1$–$C_4$ lower alkyl group, or a $C_1$–$C_{12}$ acyloxy group which may have a phenyl group, a naphthyl group or a benzyl group; or $R^2$ is a hydroxy group which reversibly forms an aldehyde group through shifting of the position of the double bond adjacent said hydroxy group;

in a hydrophilic solvent in the presence of a ruthenium compound.

The diene compound of the invention may have a structure represented by the following general formula (IX):

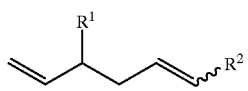

(IX)

wherein R¹ represents a hydrogen atom, a $C_1$–$C_6$ alkyl group which may have a substituent or a $C_2$–$C_6$ alkenyl group which may have a substituent; R² represents a phenyl group which may have a $C_1$–$C_4$ lower alkyl group or a $C_1$–$C_{12}$ acyloxy group which may have a phenyl group, a naphthyl group or a benzyl group; or R² is a hydroxy group which reversibly forms an aldehyde group through shifting of the position of the double bond adjacent said hydroxy group; and the wavy line shows cis-isomer, trans-isomer, or a mixture thereof.

In the above structure, R² is preferably a $C_1$–$C_{12}$ acyloxy group which may have a phenyl group, a naphthyl group or a benzyl group.

There is further provided a process for producing 4-methyl-5-hexen-1-al represented by the general formula (X):

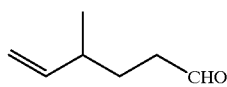

(X)

said process comprising the steps of:

a) preparing a diene compound represented by the formula (IX):

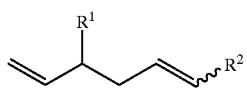

(IX)

wherein R¹ represents a methyl group; R² represents a $C_1$–$C_{12}$ acyloxy group which may have a phenyl, naphthyl or benzyl group; and the wavy line shows cis-isomer, trans-isomer, or a mixture thereof;

by reacting 2-substituted-1,3-butadienes represented by the following general formula (I):

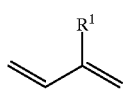

(I)

wherein R¹ represents a methyl group;

with terminal olefins represented by the following general formula (II):

(II)

wherein R² represents a $C_1$–$C_{12}$ acyloxy group which may have a phenyl group, a naphthyl group or a benzyl group; in a hydrophilic solvent in the presence of a ruthenium compound, to obtain a corresponding diene compound; and b) hydrolyzing said diene compound.

Further yet, there is provided a perfume composition at least comprising 4-methyl-5-hexen-1-al represented by the following general formula (X):

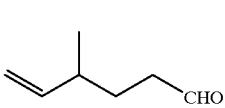

(X)

The diene compound of the invention may be 4-vinyl-8-methyl-7-nonenal represented by the formula (XI):

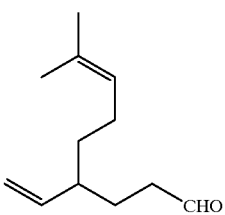

(XI)

There is also provided a perfume composition comprising, as an essential component, 4-vinyl-8-methyl-7-nonenal represented by the formula (XI):

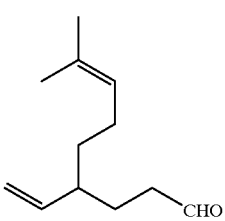

(XI)

The invention relates also to a process for producing 4-vinyl-8-methyl-7-nonenal represented by the formula (XI):

(XI)

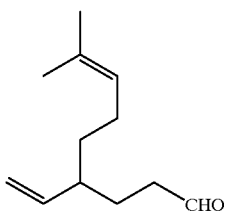

said process comprising the steps of:

a) reacting myrcene represented by the formula (VIII):

(VIII)

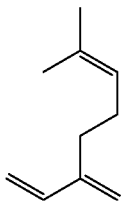

with a vinyl acylate represented by the following general formula (XII):

(XII)

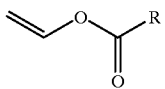

wherein R represents a hydrogen atom, a $C_1$–$C_4$ lower alkyl group or a phenyl, naphthyl or benzyl group, each of which may have a $C_1$–$C_4$ lower alkyl group; in a hydrophilic solvent in the presence of a ruthenium compound, so as to form 4-vinyl-8-methyl-1,7-nonadienyl acylate represented by the following general formula (XIII):

(XIII)

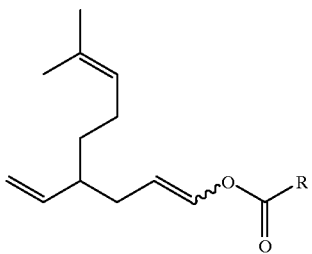

wherein R represents a hydrogen atom, a $C_1$–$C_4$ lower alkyl group or a phenyl, naphthyl or benzyl group, each of which may have a $C_1$–$C_4$ lower alkyl group; and b) hydrolyzing said 4-vinyl-8-methyl-1,7-nonadienyl acylate.

In the process for producing 4-vinyl-8-methyl-7-nonenal (XI), the ruthenium compound may comprise a ruthenium catalyst represented by the following general formula (III):

(III)

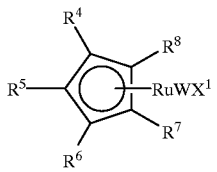

wherein $R^4$, $R^5$, $R^6$, $R^7$ and $R^8$, which may be the same or different, respectively represent a hydrogen atom or a $C_1$–$C_4$ lower alkyl group, though two adjacent groups among $R^4$, $R^5$, $R^6$, $R^7$ and $R^8$ may be bonded to each other so as to form a five- or six-membered ring; W represents 1,3-butadiene, isoprene, myrcene, 1,5-cyclooctadiene, norbornadiene, 2,3-dimethyl-1,3-butadiene or a halogen atom; and $X^1$ represents a halogen atom.

Alternatively, the ruthenium compound may comprise a ruthenium catalyst formed by mixing a ruthenium compound represented by the following general formula (IV):

(IV)

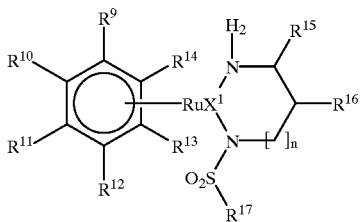

wherein $R^9$, $R^{10}$, $R^{11}$, $R^{12}$, $R^{13}$ and $R^{14}$, which may be the same or different, respectively represent a hydrogen atom or a $C_1$–$C_4$ lower alkyl group, though two adjacent groups among $R^9$, $R^{10}$, $R^{11}$, $R^{12}$, $R^{13}$ and $R^{14}$ may be bonded to each other so as to form a five- or six-membered ring; $X^1$ represents a halogen atom; $R^{15}$ and $R^{16}$ respectively represent a hydrogen atom, a $C_1$–$C_4$ lower alkyl group, a $C_5$–$C_7$ cycloalkyl group, or a phenyl, naphthyl or benzyl group, each of which may be substituted with a $C_1$–$C_4$ lower alkyl group or with a halogen atom, or $R^{15}$ and $R^{16}$ are combined with each other so as to form a $C_3$–$C_6$ alkylene group; $R^{17}$ represents a hydrogen atom, a $C_1$–$C_4$ lower alkyl group, a $C_5$–$C_7$ cycloalkyl group, a lower alkyl halide group, or a phenyl, naphthyl or benzyl group, each of which may be substituted with a $C_1$–$C_4$ lower alkyl group or with a halogen atom; and n denotes 0 or 1;

with salts represented by the following general formula (V):

$$M(X^2)_a \qquad (V)$$

wherein M represents a mono-, di- or tri-cation such as an alkaline metal, an alkaline earth metal, ammonium, silver, aluminum, lanthanum or samarium; $X^2$ represents a anion such as $ClO_4^{-1}$, $BF_4^{-1}$, $PF_6^{-1}$, $BPh_4^{-1}$ (where Ph represents a phenyl group), $CF_3SO_2O^{-1}$, $CH_3SO_2O^{-1}$, $C_4H_9SO_2O^{-1}$, $C_6H_5SO_2O^{-1}$, $4\text{-}CH_3C_6H_4SO_2O^{-1}$ or $4\text{-}ClC_6H_4SO_2O^{-1}$; a denotes 1 when M is a mono-cation, 2 when M is a di-cation or 3 when M is a tri-cation.

Alternatively yet, the ruthenium compound may comprise a ruthenium catalyst formed by mixing a ruthenium compound represented by the following general formula (VI):

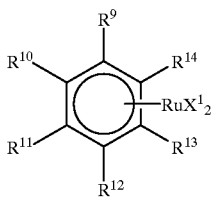

(VI)

wherein $R^9$, $R^{10}$, $R^{11}$, $R^{12}$, $R^{13}$, $R^{14}$ and $X^1$ are the same as defined above;
with salts represented by the following general formula (V):

$$M(X^2)_a \quad (V)$$

wherein M, $X^2$ and a are the same as defined above.

In the process for producing 4-vinyl-8-methyl-7-nonenal, a nitrogen bidentate ligand represented by the following general formula (VII):

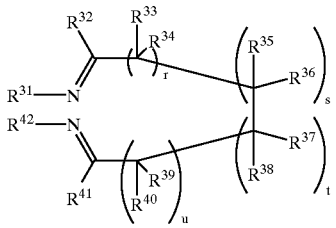

(VII)

wherein $R^{31}$ and $R^{42}$, which may be the same or different, respectively represent an aryl group which may have a $C_1$–$C_4$ lower alkyl group, a $C_1$–$C_4$ lower alkyl group, an aralkyl group or a $C_2$–$C_4$ lower alkenyl group; $R^{32}$ and $R^{41}$, which may be the same or different, respectively represent an aryl group which may have a $C_1$–$C_4$ lower alkyl group, a $C_1$–$C_4$ lower alkyloxy group which may have a substituent or a hydrogen atom; $R^{31}$ and $R^{32}$ or $R^{41}$ and $R^{42}$ may form a ring which may include an oxygen atom; r, s, t and u respectively denote 0 or 1; and $R^{33}$ to $R^{40}$ which may be the same or different, respectively represent a hydrogen atom, a $C_1$–$C_4$ lower alkyl group or a $C_2$–$C_4$ lower alkenyl group, though any two groups among $R^{33}$ to $R^{40}$ may be bonded to each other so as to form a five-or six-membered ring which may have substituents;
may be added to the ruthenium catalyst formed by mixing a ruthenium compound represented by the following general formula (VI):

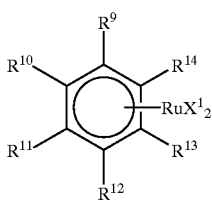

(VI)

wherein $R^9$, $R^{10}$, $R^{11}$, $R^{12}$, $R^{13}$, $R^{14}$ and $X^1$ are the same as defined above;
with salts represented by the following general formula (V):

$$M(X^2)_a \quad (V)$$

wherein M, $X^2$ and a are the same as defined above; so that the activity of said ruthenium catalyst can be controlled.

DETAILED DESCRIPTION OF THE PREFERRED EMBODIMENTS

The above and other objects, features and advantages of the present invention will be made apparent from the following description of the preferred embodiments, given as non-limiting examples.

Typical examples of the $C_1$–$C_6$ alkyl group, represented by $R^1$ in the diene compound (IX) of the present invention, include a methyl group, ethyl group, propyl group, isopropyl group, butyl group, isobutyl group, sec-butyl group, tert-butyl group, pentyl group and hexyl group. Examples of the substituent for these groups may include $C_1$–$C_4$ lower alkyl groups such as a methyl group, ethyl group, propyl group, isopropyl group, butyl group, isobutyl group, sec-butyl group and tert-butyl group; $C_1$–$C_4$ lower alkoxy groups such as a methoxy group, ethoxy group, propoxy group, isopropoxy group, butoxy group and tert-butoxy group; $C_1$–$C_{12}$ acyloxy groups, which may have a phenyl group, a naphthyl group or a benzyl group, such as a formyloxy group, acetoxy group, propanoyloxy group, butanoyloxy group, pivaloyloxy group, pentanoyloxy group, phenylacetoxy group, acetoactoxy group, benzoyloxy group and naphthoyloxy group; and $C_1$–$C_{12}$ alkoxycarboxy groups which may have a phenyl group or a naphthyl group, such as a methoxycarboxy group, ethoxycarboxy group and phenoxycarboxy group.

Typical examples of the $C_2$–$C_6$ alkenyl group represented by $R^1$ include a vinyl group, propenyl group, butenyl group, pentenyl group, hexenyl group and 4-methyl-3-pentenyl group. Further, examples of the substituent for the alkenyl group include $C_1$–$C_4$ lower alkyl groups such as a methyl group, ethyl group, propyl group, isopropyl group, butyl group, isobutyl group, sec-butyl group and tert-butyl group; $C_1$–$C_4$ lower alkoxy groups such as a methoxy group, ethoxy group, propoxy group, isopropoxy group, butoxy group and tert-butoxy group; $C_1$–$C_{12}$ acyloxy groups, which may have a phenyl group, a naphthyl group or a benzyl group, such as a formyloxy group, acetoxy group, propanoyloxy group, butanoyloxy group, pivaloyloxy group, pentanoyloxy group, phenylacetoxy group, acetoactoxy group, benzoyloxy group and naphthoyloxy group; and $C_1$–$C_{12}$ alkoxycarboxy groups, which may have a phenyl, naphthyl or benzyl group, such as a methoxycarboxy group, ethoxycarboxy group and phenoxycarboxy group.

Preferably, the group represented by $R^1$ in the diene compound (IX) include a hydrogen atom, methyl group, ethyl group, 4-methylpentyl group, 4-methyl-3-pentenyl group and 4-acetoxy-4-methylpentyl group.

As substituents of the phenyl group represented by $R^2$ in the diene compound (IX), $C_1$–$C_4$ lower alkyl groups may include a methyl group, ethyl group, propyl group, isopropyl group, butyl group, isobutyl group, sec-butyl group, and tert-butyl group.

Also in $R^2$, examples of the $C_1$–$C_{12}$ acyloxy group which may have a phenyl group, a naphthyl group or a benzyl group may include a formyloxy group, acetoxy group, propanoyloxy group, butanoyloxy group, pivaloyloxy group, pentanoyloxy group, phenylacetoxy group, acetoactoxy group, benzoyloxy group and naphthoyloxy group.

Preferable examples among the diene compounds (IX) of the invention include a compound (IX) represented by the following general formula:

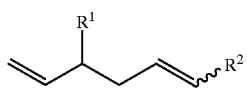

wherein $R^1$ is the same as defined above and $R^2$ represents a $C_1$–$C_{12}$ acyloxy group which may have a phenyl group, a naphthyl group or a benzyl group or $R^2$ is a hydroxy group which reversibly forms an aldehyde group through shifting of the position of the double bond adjacent to said hydroxy group.

The compound (IX) gives a higher yield in a vinyl ester reaction, compared with the compounds in which the group $R^2$ is a phenyl group which may have a $C_1$–$C_4$ lower alkyl group.

In the diene compounds (IX), the double bond may give rise to either trans-isomers, cis-isomers or a mixture thereof, and all types can be used. However, the preferred type is cis-isomers.

The diene compound (IX) of the invention is produced by reacting 2-substituted-1,3-butadienes (I) with terminal olefins (II) in the presence of a ruthenium compound in a hydrophilic solvent according to the following chemical formula:

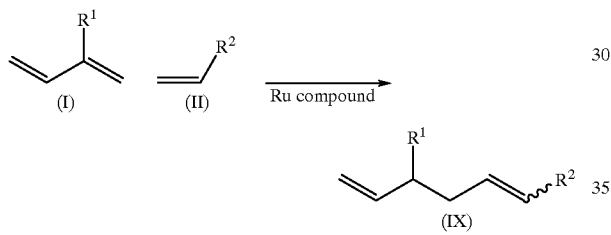

wherein $R^1$ and $R^2$ are the same as defined supra.

In the preparation of diene compound (IX), the terminal olefins (II) may generally be reacted in an amount of about 0.05 to 50 equivalents, preferably about 0.1 to 10 equivalents, relative to one equivalent of 2-substituted-1,3-butadienes (I).

The amount of ruthenium compound used in the reaction generally ranges from about 0.001 to 50 mol %, preferably from about 0.08 to 10 mol %, based on 2-substituted-1,3-butadiens (I).

The above reaction is generally carried out at about 0 to 200° C., preferably about 70 to 120° C., generally for about 1 to 72 hours, preferably about 5 to 24 hours. These conditions may be appropriately modified depending on materials subjected to the reaction and amount of the ruthenium compound. Although the reaction is usually conducted in an atmosphere of inert gas such as nitrogen gas or argon gas, it may also be conducted in an atmosphere of gasified starting material. The reaction may be carried out in a batch or continuous process.

The hydrophilic solvents to be used in the reaction include any inert solvent as far as it does not participate in the reaction. Preferably used are water, lower alcohols such as methanol, ethanol, propanol, isopropanol and butanol or amides such as dimethylformamide, dimethylacetamide, dimethylimidazolidinone and N-methylpyrrolidone or a mixture thereof. Among these solvents, methanol, ethanol, aqueous ethanol and the like are more preferred. The hydrophilic solvent is generally used in a weight ratio of 0.1 to 25 parts, preferably 0.8 to 3 parts, relative to one part of 2-substituted-1,3-butadienes (I).

Preferred examples of 2-substituted-1,3-butadiens (I), which are one of the starting materials for diene compound (IX), include butadiene, 2-methylbutadiene (isoprene), 7-methyl-3-methylene-1-octene,2-methyl-6-methylene-7-octen-2-yl acetate (myrcenyl acetate), 2-methyl-6-methylene-7-octen-2-yl methyl carbonate and 7-methyl-3-methylene-1,6-octadiene (myrcene)

Preferred examples of the terminal olefins (II), which are the counter-part starting material, are styrene, vinyl acetate, vinyl butyrate, vinyl pivalate and vinyl benzoate. In order to obtain more preferable compounds (IX) among the diene compounds (IX) of the invention, terminal olefins represented by the general formula (II) may be used in place of the terminal olefins represented by the general formula (II).

Preferred examples of the ruthenium compound used for the production of diene compound (IX) comprise the ruthenium catalysts represented by the general formula (III).

Another preferred type of ruthenium catalysts are prepared by mixing a ruthenium compound represented by the following general formula (IV), or a ruthenium compound represented by the general formula (VI), with salts represented by the general formula (V).

The ruthenium catalyst (III) used in the above reaction includes ligands. One of them has the following general formula (XIV):

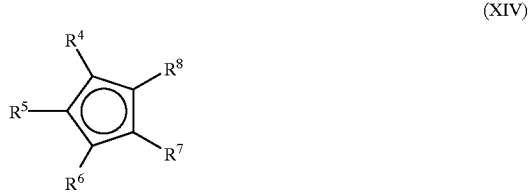

wherein $R^4$, $R^5$, $R^6$, $R^7$ and $R^8$ are the same as defined above.

Specific examples of $R^4$, $R^5$, $R^6$, $R^7$ and $R^8$ of the compound include a hydrogen atom or $C_1$–$C_4$ lower alkyl groups such as a methyl group, ethyl group, propyl group, isopropyl group, butyl group, isobutyl group, sec-butyl group, and tert-butyl group.

Preferred examples of the ligand (III), include cyclopentadienyl, tetramethylcyclopentadienyl, pentamethylcyclopentadienyl and indenyl.

Examples of the group W in the general formula (III) include 1,3-butadiene, isoprene, myrcene, 1,5-cyclooctadiene, norbornadiene, 2,3-dimethyl-1,3-butadiene, and a halogen atom which comprises a fluorine atom, chlorine atom, bromine atom and iodine atom.

Specific examples of the ruthenium compound of the formula (III) include the compounds below, in which "$\eta^m$" indicates the number of coordinate electrons, m being their number (for instance, "$\eta^6$" means that the number of coordinate electrons is 6):

($\eta^5$-cyclopentadienyl)ruthenium (III) dichloride;
($\eta^5$-cyclopentadienyl)ruthenium (III) dibromide;
($\eta^5$-cyclopentadienyl) ($\eta^4$-1,3-butadiene)ruthenium (II) chloride;
($\eta^5$-cyclopentadienyl) ($\eta^4$-isoprene)ruthenium (II) chloride;
($\eta^5$-cyclopentadienyl) ($\eta^4$-myrcene)ruthenium (II) chloride;
($\eta^5$-cyclopentadienyl) ($\eta^4$-1,5-cyclooctadiene)ruthenium (II) chloride;
($\eta^5$-cyclopentadienyl) ($\eta^4$-norbornadiene)ruthenium (II) chloride;

($\eta^5$-cyclopentadienyl) ($\eta^4$-2,3-dimethyl-1,3-butadiene) ruthenium (II) chloride;
($\eta^5$-pentamethylcyclopentadienyl)ruthenium (III) dichloride;
($\eta^5$-pentamethylcyclopentadienyl)ruthenium (III) dibromide;
($\eta^5$-pentamethylcyclopentadienyl) ($\eta^4$-1,3-butadiene) ruthenium (II) chloride;
($\eta^5$-pentamethylcyclopentadienyl) ($\eta^4$-isoprene)ruthenium (II) chloride;
($\eta^5$-pentamethylcyclopentadienyl) ($n^4$-myrcene)ruthenium (II) chloride;
($\eta^5$-pentamethylcyclopentadienyl) ($\eta^4$-1,5-cyclooctadiene) ruthenium (II) chloride;
($\eta^5$-pentamethylcyclopentadienyl) ($\eta^4$-norbornadiene) ruthenium (II) chloride; and
($\eta^5$-pentamethylcyclopentadienyl) ($\eta^4$-2,3-dimethyl-1,3-butadiene)ruthenium (II) chloride.

The ruthenium compound represented by the general formula (III) may be prepared according to a method described by K. Masuda et al. in *Organometallics*, Vol. 12, pp. 2221, 1993, a method disclosed in "Jikken Kagaku Kouza, Fourth Edition" Vol. 18, *Organometallic Complex*, pp. 269, 1991, edited by Japan Society of Chemical Engineers and published by Maruzen, or by other similar methods.

For instance, ($\eta^5$-pentamethylcyclopentadienyl) ($\eta^4$-isoprene) ruthenium (II) chloride can be synthesized by the following method:

Pentamethylcyclopentadienyl ruthenium (II) dichloride dimer and one equivalent of zinc powder are suspended in methanol (100 times the amount of the ruthenium complex) at 0° C. Then, 30 equivalents of isoprene are added to the suspension. After the mixture is reacted for 15 minutes, a solid portion is separated by filtration. The resulting solution is concentrated to obtain a crude product. The crude product is recrystallized from ethanol to yield ($\eta^5$-pentamethylcyclopentadienyl) ($\eta^4$-isoprene) ruthenium (II) chloride.

The above method may be utilized to prepare ruthenium compounds represented by the general formula (III), other than for ($\eta^5$-pentamethylcyclopentadienyl) ($\eta^4$-isoprene) ruthenium (II) chloride.

The ruthenium compound represented by the general formula (IV) or (VI) used in the inventive reaction includes a plurality of ligands. One of them has a structure represented by the following general formula (XV):

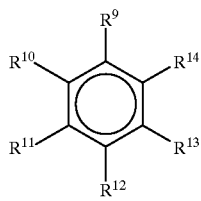

(XV)

wherein $R^9$, $R^{10}$, $R^{11}$, $R^{12}$, $R^{13}$ and $R^{14}$ are the same as defined above.

Specific examples of $R^9$, $R^{10}$, $R^{11}$, $R^{12}$, $R^{13}$ or $R^{14}$ include a hydrogen atom and lower alkyl groups such as a methyl group, ethyl group, propyl group, isopropyl group, butyl group, isobutyl group, sec-butyl group and tert-butyl group.

Preferred examples of the ligand (XV) include benzene, p-cymene, mesitylene and hexamethylbenzene.

One of the ligands in the ruthenium compound of the general formula (IV) is represented by the following general formula (XVI):

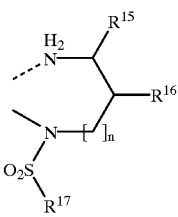

(XVI)

wherein $R^{15}$, $R^{16}$, $R^{17}$ and n are the same as defined above.

Specific examples of the group $R^{15}$ or $R^{16}$ include a hydrogen atom, $C_1$–$C_4$ lower alkyl groups such as a methyl group, ethyl group, propyl group, isopropyl group, butyl group, isobutyl group, sec-butyl group and tert-butyl group; $C_5$–$C_7$ cycloalkyl groups such as a cyclopentyl group, cyclohexyl group and cycloheptyl group; phenyl groups which may be substituted with a $C_1$–$C_4$ lower alkyl group or a halogen atom, (where examples of the $C_1$–$C_4$ lower alkyl groups include a methyl group, ethyl group, propyl group, isopropyl group, butyl group, isobutyl group, sec-butyl group and tert-butyl group and examples of the halogen atoms include a fluorine atom, chlorine atom, bromine atom and iodine atom); naphthyl groups which may be substituted with a $C_1$–$C_4$ lower alkyl group or a halogen atom, where examples of the $C_1$–$C_4$ lower alkyl groups or the halogen atoms are the same as above; and benzyl groups which may be substituted with a $C_1$–$C_4$ lower alkyl group or a halogen atom, where examples of the $C_1$–$C_4$ lower alkyl groups or the halogen atoms are the same as above. Alternatively, $R^{15}$ and $R^{16}$ may be combined with each other to form an alkylene group having 3–6 carbon atoms, where examples of the alkylene group having 3–6 carbon atoms include 1,3-propylene, 1,4-butylene, 1,5-pentylene and 1,6-hexelene.

Specific examples of the group $R^{17}$ in the ligand (XVI) include a hydrogen atom and $C_1$–$C_4$ lower alkyl groups such as a methyl group, ethyl group, propyl group, isopropyl group, butyl group, isobutyl group, sec-butyl group and tert-butyl group; $C_5$–$C_7$ cycloalkyl groups such as a cyclopentyl group, cyclohexyl group and cycloheptyl group; lower alkyl halides such as a trifluoromethyl group and trichloromethyl group; phenyl, naphthyl and benzyl groups, each of which may be substituted with a $C_1$–$C_4$ lower alkyl group or a halogen atom, where examples of the $C_1$–$C_4$ lower alkyl groups include a methyl group, ethyl group, propyl group, isopropyl group, butyl group, isobutyl group, sec-butyl group and tert-butyl group and examples of the halogen atoms include a fluorine atom, chlorine atom, bromine atom and iodine atom.

Preferred examples of the ligand (XVI) include N-2-aminoethyl-methanesulfonamide, N-2-aminoethyl-benzenesulfonamide, N-2-aminoethyl-p-toluenesulfonamide, N-2-aminoethyl-trifluoro methanesulfonamide, N-2-aminoethyl-trichloromethanesulfonamide, N-3-aminopropyl-methane sulfonamide, N-3-aminopropyl-benzenesulfonamide, N-3-aminopropyl-p-toluenesulfonamide, N-3-aminopropyl-trifluoromethanesulfonamide, N-3-aminopropyl-trichloromethanesulfonamide, N-2-amino-1,2-dimethylethyl-methanesulfonamide, N-2-amino-1,2-dimethylethyl-benzenesulfonamide, N-2-amino-1,2-dimethylethyl-p-toluenesulfonamide, N-2-amino-1,2-dimethylethyl-trifluoromethanesulfonamide, N-2-amino-1,2-dimethylethyl-trichloromethane sulfonamide, N-2-amino- 1,2-diphenylethyl-methanesulfonamide, N-2-amino-1,2-diphenylethyl-benzene sulfonamide, N-2-amino-1,2-diphenylethyl-p-toluenesulfonamide, N-2-amino-1,2-diphenylethyl-trifluoromethanesulfonamide, N-2-amino-1,2-diphenylethyl-trichloromethanesulfonamide, 2-methanesulfonylamino-cyclohexylamine, 2-benzene sulfonylamino-cyclohexylamine, 2-p-toluenesulfonylamino-cyclohexylamine, 2-trifluoro methanesulfonylamino-cyclohexylamine and 2-trichloromethanesulfonylamino-cyclohexylamine.

$X^1$ in the compound (IV) or (VI) is a halogen atom. Specific examples of the halogen atom may include a fluorine atom, chlorine atom, bromine atom and iodine atom.

Specific examples of the ruthenium compound represented by the general formula (IV) include the compounds below, in which "$\eta^m$" indicates the number of coordinate electrons, m being their number:

(N-2-aminoethyl-p-toluenesulfonamide) ($\eta^6$-benzene) ruthenium (II) chloride;
(N-2-aminoethyl-p-toluenesulfonamide) ($\eta^6$-p-cymene) ruthenium (II) chloride;
(N-2-aminoethyl-p-toluenesulfonamide) ($\eta^6$-mesitylene) ruthenium (II) chloride;
(N-2-aminoethyl-p-toluenesulfonamide) ($\eta^6$-benzene) ruthenium (II) bromide;
(N-2-aminoethyl-p-toluenesulfonamide) ($\eta^6$-p-cymene) ruthenium (II) bromide; and
(N-2-aminoethyl-p-toluenesulfonamide) ($\eta^6$-mesitylene) ruthenium (II) bromide.

The ruthenium compound represented by the general formula (IV) may be produced according to a well-known method (for instance, the method described in WO97/20789) or the methods supra.

For instance, (N-2-aminoethyl-p-toluene sulfonamide) (aryl)ruthenium (II) chloride may be synthesized by the following method:

($\eta^6$-Benzene))ruthenium (II) dichloride and one equivalent of N-2-aminoethyl-p-toluene sulfonamide are heated and stirred at 80° C., together with isopropyl alcohol. The resulting mixture is then concentrated and washed to obtain (N-2-aminoethyl-p-toluenesulfonamide) ($\eta^6$-benzene) ruthenium (II) dichloride.

The above method may be utilized to obtain the ruthenium compounds represented by the general formula (IV), other than for (N-2-aminoethyl-p-toluenesulfonamide) (aryl)ruthenium (II) chloride.

As specific examples of the ruthenium compound of the general formula (VI), the following compounds may be given.

Ruthenium $\eta^6$-benzene dichloride
Ruthenium $\eta^6$-p-cymene dichloride
Ruthenium $\eta^6$-mesitylene dichloride
Ruthenium $\eta^6$-benzene dibromide
Ruthenium $\eta^6$-p-cymene dibromide
Ruthenium $\eta^6$-mesitylene dibromide
Ruthenium $\eta^6$-benzene diiodide
Ruthenium $\eta^6$-p-cymene diiodide
Ruthenium $\eta^6$-mesitylene diiodide On the other hand, the salts represented by the general formula (V) form the ruthenium catalyst in combination with the ruthenium compound represented by the general formula (IV) or (VI). In the formula (V), M represents a mono-, di- or tri-cation such as alkaline metals, alkaline earth metals, ammonium, silver, aluminum, lanthanum or samarium. Specific examples of these cations include $Li^+$, $Na^+$, $K^+$, $Mg^{2+}$, $Ca^{2+}$, $NH_4^+$, $Ag^+$, $Al^{3+}$, $La^{3+}$ and $Sm^{3+}$. Specific examples of $X^2$ which represents anions may include $C_{104}^-$, $BF_4^-$, $PF_6^-$, $BPh_4^-$, (where Ph represents a phenyl group), $CF_3SO_2O^-$, $CH_3SO_2O^-$, $C_6H_5SO_2O^-$, $4\text{-}CH_3C_6H_4SO_2O^-$ and $4\text{-}ClC_6H_4SO_2O^-$.

The ruthenium catalyst is formed by mixing the ruthenium compound of the general formula (IV) or (VI) with the salts of the general formula (V) in an appropriate reaction system.

Preferably, to the ruthenium catalyst system formed from the ruthenium compound of the formula (IV) or (VI) and the salts of the formula (V) is added a nitrogen bidentate ligand represented by the general formula (VII).

The addition of this nitrogen bidentate ligand further improves the activity of the ruthenium catalyst, and the objective product can be obtained more economically than when the foregoing ruthenium catalyst is used.

In the nitrogen bidentate ligand (VII), specific examples of the groups $R^{31}$ to $R^{42}$ include $C_1$–$C_4$ lower alkyl groups such as a methyl group and ethyl group, aryl groups such as a phenyl group and tolyl group and alkoxy groups such as a methoxy group and ethoxy group. $R^{31}$ and $R^{32}$ or $R^{41}$ and $R^{42}$ may be bonded to each other to form, a pyridine ring, an oxazoline ring or the like. Moreover, any two groups among $R^{33}$ to $R^{40}$ may be bonded to each other, whereby the moiety linking imine groups may form a ring such as a phenyl, naphthyl or benzyl group.

More specific examples of the nitrogen bidentate ligand (VII) include 2,2-piperidine, 2,2'-bis(4-benzyl-2-oxazoline), 2,2'-bis[(2-oxazolinyl)naphthyl] and 2,2'-methylenebis(4-phenyl-2-oxazoline).

In the preparation process of the diene compound (IX), previously prepared ruthenium compound may be used as a catalyst. Alternatively, the starting materials of ruthenium compound may be added separately to the reaction system.

In the second aspect of the invention, 4-methyl-5-hexen-1-al of the formula (X) can be easily obtained at low costs by hydrolyzing a compound of the formula (IX). 4-Methyl-5-hexen-1-al has a fragrance that is easily diffusible and gives a highly fresh and green fruit-like scent. This fragrance is milder, less irritating and more fruity than similar perfume compounds such as cis-3-hexenal and trans-2-hexenal.

The invention also relates to a process for producing 4-methyl-5-hexen-1-al of the general formula (X).

The process comprises hydrolyzing a diene compound of the formula (IX).

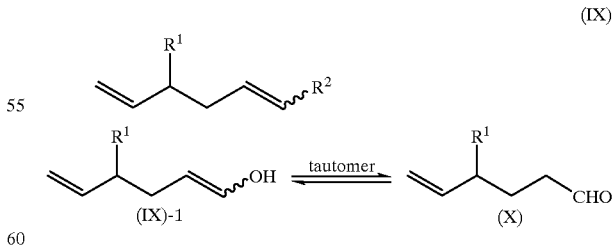

Further, there is provided a perfume composition comprising 4-methyl-5-hexen-1-al of the formula (X).

The diene compound of the formula (IX) can be synthesized from isoprene (I) and a vinyl acylate compound (II) in the presence of a ruthenium catalyst as shown in the reaction below:

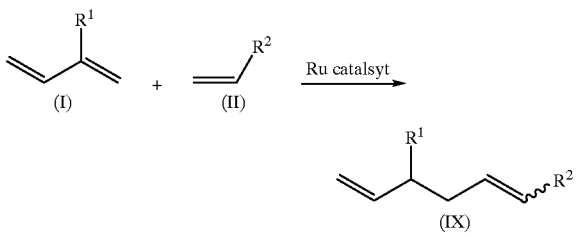

In the vinyl acylate compound of the formula (II), $R^2$ is a $C_1$–$C_{12}$ acyloxy group which may have a phenyl, naphthyl or benzyl group or $R^2$ is a hydroxy group which reversibly forms an aldehyde group through shifting of the position of the double bond adjacent to said hydroxy group.

Examples of the $C_1$–$C_{12}$ acyloxy group (which may have a phenyl, naphthyl or benzyl group) may include a formyloxy group, acetoxy group, propanoyloxy group, butanoyloxy group, pivaloyloxy group, pentanoyloxy group, phenyl acetoxy group, acetoacetoxy group, benzoyloxy group or naphthoyloxy group.

Preferred examples of the vinyl acylate compound include vinyl acetate, vinyl butylate, vinyl pivalate and vinyl benzoate.

In the diene compound (IX) which is the starting material of the present invention, R is a $C_1$–$C_{12}$ acyloxy group which may have a phenyl, naphthyl or benzyl group.

Examples of the $C_1$–$C_{12}$ acyloxy group (which may have a phenyl, naphthyl or benzyl group) may include a formyloxy group, acetoxy group, propanoyloxy group, butanoyloxy group, pivaloyloxy group, pentanoyloxy group, phenyl acetoxy group, acetoacetoxy group, benzoyloxy group or naphthoyloxy group.

Preferred examples of the diene compound (IX) are 4-methyl-1,5-hexadien-1-yl acetate, 4-methyl-1,5-hexadien-1-yl butanoate, 4-methyl-1,5-hexadien-1-yl pivalate and 4-methyl-1,5-hexadien-1-yl benzoate.

The ruthenium compound represented by the general formula (IV) may be produced according to a well-known method, e.g. method described in WO97/20789, or a method supra.

The solvent used in the co-dimerization reaction of isoprene (I) with the vinyl acylate compound (II) may include any inert solvent as far as it does not participate in the reaction. Hydrophilic solvents including water, lower alcohols such as methanol, ethanol, propanol, isopropanol and butanol or amides such as dimethylformamide, dimethylacetamide, dimethyl-imidazolidinone and N-methylpyrrolidone or a mixture of these solvents may preferably be used. Among them, methanol, ethanol, aqueous methanol and aqueous ethanol and the like are the preferred solvents.

The hydrophilic solvent is generally used in a ratio of about 0.1 to 25 parts by volume, preferably 0.8 to 3 parts by volume, relative to one part by weight of isoprene.

In the co-dimerization reaction, the content of the vinyl acylate compound (II) is generally 0.05 to 50 equivalents, preferably 0.1 to 10 equivalents, relative to one equivalent of isoprene.

In the co-dimerization reaction, the content of the ruthenium compound to be used is about 0.001 to 50 equivalents, preferably about 0.08 to 10 equivalents, relative to one equivalent of isoprene.

The above reaction is generally carried out at about 0 to 200° C., preferably about 70 to 120° C. for about 1 to 72 hours, preferably about 5 to 24 hours. These conditions may be appropriately modified, depending upon the materials subjected to the reaction and the content of the ruthenium compound.

Although the reaction is usually conducted in an atmosphere of inert gas such as nitrogen gas or argon gas, it may also be conducted in an atmosphere of gasified starting material.

In the diene compound (IX) thus obtained, the double bond is preferably cis-type, though it may be any one of trans-type, cis-type and a mixture of both.

4-Methyl-5-hexen-1-al (X) used in the present invention can be obtained with ease by hydrolyzing the diene compound (IX). According to a specific hydrolyzing method, the diene compound (IX) is heated and stirred in an aqueous sulfuric acid solution, aqueous hydrochloric acid and/or aqueous acetic acid solution. Alternatively, it can be heated, depending on the necessity, in an aqueous solution of an alkali such as sodium hydroxide.

4-Methyl-5-hexen-1-al represented by the formula (X), as described in test examples infra, has high diffusibility, a strongly fresh green fruit-like fragrance, and emanates a less irritating odor. It is fruitier and milder than similar perfume compounds such as cis-3-hexenal and trans-2-hexenal. It can therefore be used in general-purpose applications such as fruity type or floral green type perfumes, as well as additive materials for a green apple, kiwi, or apple flavor. It may also be used as adjuvant for fruit fragrances.

The perfume composition according to the present embodiment can provide aromatics, various cosmetics and sanitary materials. For instance, 4-methyl-5-hexen-1-al (X) is added to aromatics such as deodorants and interior aromatics; various cosmetics including cleaning cosmetics such as soaps, shampoos and rinses, hair cosmetics such as hair dyes and hair tonics, fundamental cosmetics such as creams, face lotions, colognes and packs, make-up cosmetics such as powders, foundations and rouges, fragrant cosmetics such as scents, sunburn or sunscreen cosmetics, lip cosmetics such as lipsticks and lip creams, oral cosmetics such as dental creams and mouth washes and bath cosmetics; sanitary materials such as disinfectants and insecticides; bleaches, softeners or tableware detergents.

4-Methyl-5-hexen-1-al (X) is added to the above products in an amount sufficient to confer fragrance to them and heighten the product value.

The content of 4-methyl-5-hexen-1-al (X) to be added in the perfume composition may be determined depending on the object. It is preferably 10 ppm to 10% by weight in the total amount, although no particular limitation is imposed on the content. The perfume composition according to the present embodiment may be supplemented with various blending perfume elements or base agents for designing fragrances.

The present invention thus enables the production of 4-methyl-5-hexen-1-al (X) with high purity in a simple process at a lower cost. This compound is highly diffusible, and has a strong and fresh green fruit-like fragrance. Moreover, the inventive compound has a less irritating odor and is fruitier and milder than the similar perfume compounds such as cis-3-hexenal and trans-2-hexenal. It can therefore be used for general-purpose applications such as fruity type or floral green type perfumes, as well as raw blending agents for green apples, kiwis, apples or the like. Also it can be used to enhance the fragrances of fruits. Therefore, the perfume composition comprising the inventive compound can be utilized in a wide range of application fields such as aromatics, various cosmetics or sanitary materials.

In a fourth aspect of the invention, there is provided 4-vinyl-8-methyl-7-nonenal. This product is a novel compound which has a high diffusibility and a strong aliphatic aldehyde-like fragrance, emanating simultaneously a citrus- and rose-like fragrance. This product can therefore be used for conferring scents to perfume compositions. These characteristics of 4-vinyl-8-methyl-7-nonenal (XI) have been hitherto unknown.

The product (XI) can be obtained in the reactions illustrated below: myrcene (VIII) is reacted with a vinyl acylate compound (XII) under a low polymerization reaction process, i.e., a co-dimerization reaction process, thereby obtaining 4-vinyl-8-methyl-1,7-nonadienyl acylate (XIII). Then, the latter is hydrolyzed to give 4-vinyl-8-methyl-7-nonenal (XI):

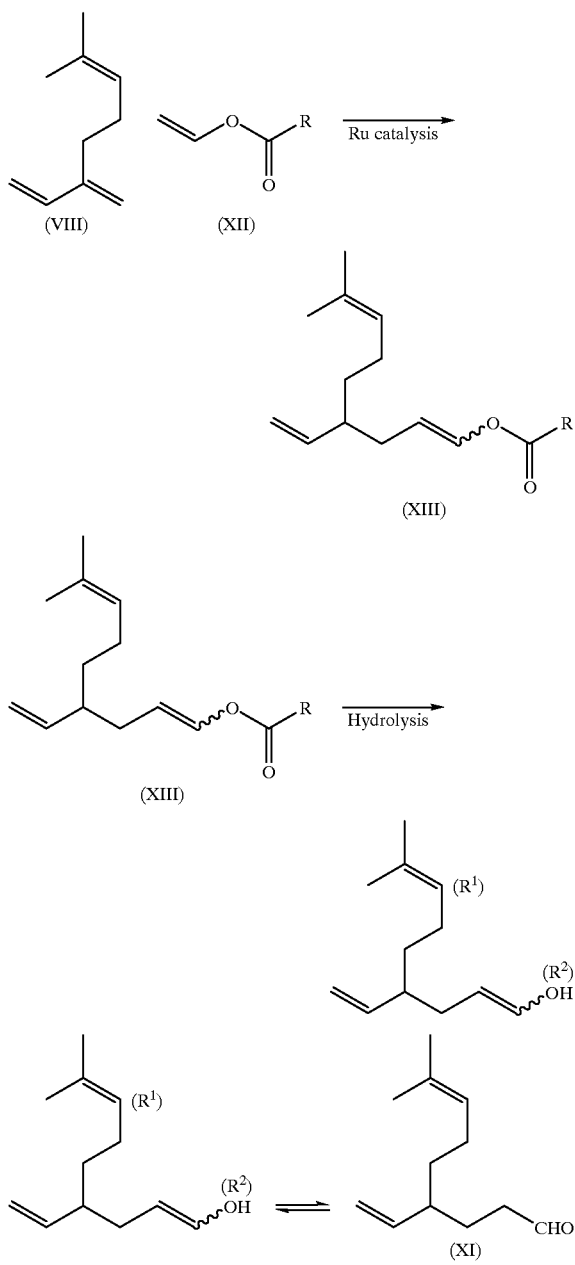

The codimerization reaction is conducted in a hydrophilic solvent, in the presence of a ruthenium catalyst.

R in the vinyl acylate compound (XII) is a hydrogen atom, a $C_1$–$C_4$ lower alkyl group or a phenyl, naphthyl or benzyl group which may have a $C_1$–$C_4$ lower alkyl group. Among these groups, specific examples of the $C_1$–$C_4$ lower alkyl group include a methyl group, ethyl group, propyl group, butyl group, isobutyl group, sec-butyl group and tert-butyl group. Examples of the $C_1$–$C_4$ lower alkyl group in the phenyl, naphthyl or benzyl group which may have the $C_1$–$C_4$ lower alkyl group include a methyl group, ethyl group, propyl group, butyl group, isobutyl group, sec-butyl group and tert-butyl group.

Preferred specific examples of the vinyl acylate compound represented by the general formula (XII) are vinyl acetate, vinyl butyrate, vinyl pivalate and vinyl benzoate.

In 4-vinyl-8-methyl-1,7-nonadienyl acylate (XIII) which is obtained as the intermediate for the present invention, R is a hydrogen atom, $C_1$–$C_4$ lower alkyl group or phenyl, naphthyl or benzyl group which may have a $C_1$–$C_4$ alkyl group.

Preferred specific examples of 4-vinyl-8-methyl-1,7-nonadienyl acylate represented by the general formula (XIII) include 4-vinyl-8-methyl-1,7-nonadienyl acetate, 4-vinyl-8-methyl-1,7-nonadienyl propionate, 4-vinyl-8-methyl-1,7-nonadienylbutyrate, 4-vinyl-8-methyl-1,7-nonadienyl pivalate and 4-vinyl-8-methyl-1,7-nonadienyl benzoate.

In the production of 4-vinyl-8-methyl-1,7-nonadienyl acylate (XIII), the vinyl acylate compound (XII) may be reacted generally in an amount of about 0.05 to 50 equivalents, preferably 0.1 to 10 equivalents, relative to one equivalent of myrcene (VIII).

The content of the ruthenium compound used in this reaction ranges from about 0.001 to 50 mol %, preferably from about 0.8 to 10 mol %, based on one mol of myrcene (VIII).

The above reaction is carried out generally at about 0 to 200° C., preferably about 70 to 120° C., for about 1 to 72 hours, preferably about 5 to 24 hours. These conditions may be appropriately modified depending upon the materials subjected to the reaction and the amount of ruthenium compound. Although the reaction is usually conducted in an atmosphere of inert gas such as nitrogen gas or argon gas, it may also be conducted in an atmosphere of gasified starting material. Further, the reaction may be conducted in a batch or continuous process.

The hydrophilic solvent used in the above reaction may include any inert solvent, as far as it does not participate in the reaction. Preferably used hydrophilic solvents include water, lower alcohols such as methanol, ethanol, propanol, isopropanol and butanol or amides such as dimethylformamide, dimethylacetamide, dimethylimidazolidinone and N-methylpyrrolidone or a mixture of these solvents. Among them, methanol, ethanol, aqueous ethanol and the like are more preferably used. The hydrophilic solvent is used in a ratio ranging generally from 0.1 to 25 parts by volume, preferably from 0.8 to 3 parts by volume, relative to one part by weight of myrcene (VIII).

After the reaction is completed, the resultant reaction mixture is treated in a usual way. Then, the resulting mixture is distilled to extract 4-vinyl-8-methyl-1,7-nonadienyl acylate (XIII) as an intermediate.

To prepare 4-vinyl-8-methyl-1,7-nonadienyl acylate (XIII), a ruthenium compound can be used. Preferred examples of the ruthenium compound include ruthenium catalyst represented by the following general formula (III) supra.

Another preferred ruthenium catalyst is prepared by mixing a ruthenium compound having the formula (IV) and a salt having the formula (V) supra.

R in the vinyl acylate compound (XII) is a hydrogen atom, a $C_1$–$C_4$ lower alkyl group or a phenyl, naphthyl or benzyl group which may have a $C_1$–$C_4$ lower alkyl group. Among these groups, specific examples of the $C_1$–$C_4$ lower alkyl group include a methyl group, ethyl group, propyl group, butyl group, isobutyl group, sec-butyl group and tert-butyl group. Examples of the $C_1$–$C_4$ lower alkyl group in the phenyl, naphthyl or benzyl group which may have the $C_1$–$C_4$ lower alkyl group include a methyl group, ethyl group, propyl group, butyl group, isobutyl group, sec-butyl group and tert-butyl group.

Preferred specific examples of the vinyl acylate compound (XII) include vinyl acetate, vinyl butyrate, vinyl pivalate and vinyl benzoate.

In 4-vinyl-8-methyl-1,7-nonadienyl acylate (XIII) obtained as the intermediate, R is a hydrogen atom, $C_1$–$C_4$ lower alkyl group or a phenyl, naphthyl or benzyl group which may have a $C_1$–$C_4$ alkyl group.

Preferred specific examples of 4-vinyl-8-methyl-1,7-nonadienyl acylate (XIII) include 4-vinyl-8-methyl-1,7-nonadienyl acetate, 4-vinyl-8-methyl-1,7-nonadienyl propionate, 4-vinyl-8-methyl-1,7-nonadienyl butyrate, 4-vinyl-8-methyl-1,7-nonadienyl pivalate and 4-vinyl-8-methyl-1,7-nonadienyl benzoate.

Specific examples of the salts (V) include silver triflate ($CF_3SO_2OAg$), potassium nonaflate ($C_4F_9SO_2OK$), lanthanum triflate [$(CF_3SO_2O)_3La$], samarium triflate [$(CF_3SO_2O)_3Sm$] and ammonium triflate ($CF_3SO_2ONH_4$). Commercially available products may be used as it is.

To form a ruthenium catalyst from the ruthenium compound (IV) and the salts (V), the compounds (IV) and (V) may be mixed in an appropriate reaction system. The amount of salts (V) used in the reaction generally ranges from 0.5 to 10 equivalents, preferably from 1.0 to 3.0 equivalents, relative to one equivalent of the ruthenium compound.

In the preparation of the 4-vinyl-8-methyl-1,7-nonadienyl acylate (XIII), previously prepared ruthenium compounds may be used as reaction catalysts. Alternatively, the starting materials of ruthenium compound may be separately added to the reaction system, so as to catalyze the reaction.

In 4-vinyl-8-methyl-1,7-nonadienyl acylate (XIII) thus obtained, the double bond may form any one of trans-type, cis-type and a mixture of the both. However, preferred form is cis-type.

The inventive 4-vinyl-8-methyl-7-nonenal (XI) can be obtained easily by hydrolyzing 4-vinyl-8-methyl-1,7-nonadienyl acylate (XIII).

According to a specific hydrolyzing method, 4-vinyl-8-methyl-1,7-nonadienyl acylate (XIII) is heated and stirred in an aqueous acid solution such as aqueous sulfuric acid, aqueous hydrochloric acid and/or aqueous acetic acid. Alternatively, it can be heated, where necessary, in an aqueous alkali solution such as sodium hydroxide.

Examples of the acid used in the production of 4-vinyl-8-methyl-7-nonenal (XI) include mineral acids such as sulfuric acid and hydrochloric acid, and organic acids such as acetic acid. These acids may be used either alone or in an appropriate mixture thereof.

Examples of the alkali sodium include sodium hydroxide, potassium hydroxide and barium hydroxide. These alkalis may be used either alone or in an appropriate mixture thereof. The concentration of the aqueous acid or alkali solutions may be adjusted depending upon the reaction condition. In a mineral acid, an organic acid and an alkali, the preferred concentration ranges from 1 to 30% by equivalent, 1 to 5% by equivalent and 1 to 5% by equivalent, respectively.

The above hydrolysis is generally carried out at about 20 to 120° C., preferably about 30 to 100° C. for about 1 to 72 hours, preferably about 5 to 24 hours. These conditions may be appropriately modified depending upon the materials subjected to the reaction and the content of the aqueous acid or alkali solution. Although the reaction is usually conducted in an atmosphere of inert gas such as nitrogen gas or argon gas, it may also be conducted in an atmosphere of gasified starting material. The reaction may be conducted either in a batch process or in a continuous process.

Any inert solvent may be used in the above reaction, as far as it does not participate in the reaction. Commonly used solvents include water, lower alcohols such as methanol, ethanol, propanol, isopropanol and butanol or amides such as tetrahydrofuran, dimethylformamide, dimethylacetamide, dimethylimidazolidinone and N-methylpyrrolidone or a mixture of these solvents. Among them, methanol, ethanol, tetrahydrofuran and the like may be preferably used. The hydrophilic solvent is generally used in a ratio ranging from about 0.1 to 25 parts by volume, preferably from 0.8 to 3 parts by volume, relative to one part by weight of 4-vinyl-8-methyl-1,7-nonadienyl acylate (XIII).

After the reaction is completed, the resulting reaction mixture is treated in a usual way. The mixture is then distilled to extract the objective 4-vinyl-8-methyl-7-nonenal (XI).

4-Vinyl-8-methyl-7-nonenal (XI) according to the present invention has a high diffusibility and a strong aliphatic aldehyde-like fragrance, emanating simultaneously a citrus- and rose-like fragrance. When it is diluted, it exudes a sweet and milky fragrance like 1-citronellol. Therefore, it can be used in general-purpose applications such as citrus type or floral green type perfumes, as well as raw blending essences for melons, cucumbers or the like. According to the present invention, a perfume composition containing 4-vinyl-8-methyl-7-nonenal, alone or with other common perfume essences, may be used as the fragrance component.

The other perfume essences include such widespread perfume components as those described by S. Arctander in "Perfume and Flavor Chemicals", published in 1969, Montclair, N.J., U.S.A. Typical examples of the perfume are α-pinene, limonene, cis-3-hexenol, phenylethyl alcohol, styraryl acetate, eugenol, rose oxide, linalool and benzaldehyde.

The proportion of 4-vinyl-8-methyl-7-nonenal (XI) to be included in the perfume composition may be determined according to the type and purpose of perfume preparation. Preferably it is in the range of between 10 ppm and 10% by weight, based on the total amount of the perfume composition, though no particular limitation is imposed on it. Various blending perfumes and fragrance-controlling agents may be appropriately added, depending on the purpose.

The present invention enables the production of 4-vinyl-8-methyl-7-nonenal (XI) with high purity in a simple method at a low cost. This compound is a novel perfume which has a high diffusibility and a strong aliphatic aldehyde-like fragrance, emanating simultaneously a slightly citrus- and rose-like fragrance. The inventive compound can therefore be used for general-purpose applications such as citrus type or floral green type perfumes, as well as raw blending agents for melons, cucumbers or the like. Also it can be used to enhance a citrus-like fragrance. The perfume composition of the present invention comprising the inventive compound can be used in a wide range of application fields such as aromatics, various cosmetics, sanitary materials.

The diene compound of the present invention is a very important compound as an intermediate for synthesizing compounds, particularly, terpenes, which are useful for intermediates for synthesizing medicines.

According to the present invention, a low molecular weight diene compound of high purity which is superior in regioselectivity can be produced in a simple method at a low price.

EXAMPLE

The present invention will be hereinafter described in more detail by way of examples, reference examples and comparative examples, which are not intended to limit the present invention. It is needless to say that the present invention can be changed variously without departing from the technological idea of the invention.

In the examples described below, the product is measured for its chemical purity and identified according to the following methods.

(Measurement of chemical purity)

The chemical purity is measured by a gas chromatographic method (GLC). The conditions for the measurement are as follows:

Applied analytical instrument: HP5890 Series II Gas chromatograph manufactured by Hewlett Packard Column: Neutrabond-1 (NB-1;0.25 mm×30 m)

Detector: FID $^1$H-Nuclear magnetic resonance spectrum ($^1$H-NMR)

Instrument: GEMINI2000 (1H, 200 MHz), (manufactured by Varian)

Infrared absorption spectrum (IR)

Instrument: FTIR-8200 PC model (manufactured by Nippon Bunko Kogyo Kabushiki Kaisha)

Measuring method: Film (Identification of products)

The identification of the product was made using a $^1$H-NMR spectrum by comparing with data described in known literature.

Reference Example 1

Synthesis of ($\eta^5$-pentamethylcyclopentadienyl) ($\eta^4$-isoprene) ruthenium (II) chloride 200 mg (0.65 mmol as a monomer) of a ($\eta^5$-pentamethylcyclopentadienyl) ruthenium (III) dichloride dimer and 42 mg of a zinc powder were suspended in 20 ml of methanol and the suspension was cooled in an argon atmosphere in an ice-cooled bath. To the mixture was added 2 ml of isoprene and further 42 mg of zinc. The reaction mixture was stirred for one hour while it is ice-cooled, followed by filtration and concentration, to obtain 75 mg (yield: 34%) of ($\eta^5$-pentamethylcyclopentadienyl) ($\eta^4$-isoprene) ruthenium (II) chloride.

The various spectrum data of the product accorded with the value of the literature.

Reference Example 2

Synthesis of ($\eta^5$-pentamethylcyclopentadienyl)($\eta^4$-norbornadiene) ruthenium (II) chloride 270 mg of a ($\eta^5$-pentamethylcyclopentadienyl) ruthenium (II) dichloride dimer was suspended in 10 ml of methanol, to which was added 3 ml (24.5 mmol) of norbornadiene. The mixture was heated to 70° C. and stirred for one hour. After the temperature of the reaction mixture was returned to room temperature, the reaction mixture was concentrated under reduced pressure and passed through an alumina column to purify. A yellow band was collected, followed by distilling the solvent to obtain a yellowish orange solid. This solid was recrystallized from chloroform/diethyl ether to obtain 0.256 g(yield: 77%) of ($\eta^5$-pentamethylcyclopentadienyl) ($\eta^4$-norbornadiene) ruthenium (II) chloride.

The various spectrum data of the product accorded with the value of the literature.

Reference Example 3

Synthesis of (N-2-aminoethyl-p-toluenesulfonamide) ($\eta^6$-benzene) ruthenium (II) chloride 2.5 g (10 mmol) of ($\eta^6$-benzene) ruthenium (II) dichloride dimer and 2.14 g (10 mmol) of N-2-aminoethyl-p-toluenesulfonamide were heated with stirring together with 80 ml of isopropyl alcohol at 80° C. for 4 hours. The reaction mixture was concentrated and washed to obtain 4 g (yield: 93%) of (N-2-aminoethyl-p-toluenesulfonamide) ($\eta^6$-benzene) ruthenium (II) chloride.

The various spectrum data of the product accorded with the value of the literature.

Example 1

Synthesis of 4-methylhexa-1,5-dien-1-yl acetate 6.5 mg (0.020 mmol) of ($\eta^5$-pentamethylcyclopentadienyl) ($\eta^4$-isoprene) ruthenium (II) chloride obtained in the Reference Example 1, 5 ml(50 mmol) of isoprene, 5 ml (54 mmol) of vinyl acetate and 5 ml of methanol were heated with stirring at 80° C. for 15 hours in an argon atmosphere. The reaction mixture was distilled to obtain non-reacted isoprene and vinyl acetate and, in succession, 1.07 g (yield: 14% based on isoprene) of a co-dimer (4-methylhexa-1,5-dien-1-yl acetate). No distillation residue, such as polymers, was observed and the reaction proceeded selectively (purity: 91%, regioisomer: 4%, cyclic dimer of dienes: 5%).

Boiling point: 80–100° C./10 mmHg $^1$H-NMR (200 MHz, CDCl$_3$):

δ1.01(3H, d, J=6.6 Hz), 2.14(3H, s), 2.0–2.4(3H, m), 4.8–5.1(3H, m), 5.74(1H, ddd, J=6.8, 10.2, 17.2 Hz), 7.08 (1H, dm, J=6.6 Hz)

Gas chromatography analysis:

Column: NB-1 (produced by G. L. Science)

Measurement temperature: 60–250° C. (temperature was raised at a rate of 10° C./minute)

Retention time=7.29 minutes (product), 7.84 minutes (isomer), 7.53 minutes (dimer)

Example 2

Synthesis of 4-methylhexa-1,5-dien-1-yl acetate 16.5 mg (0.038 mmol) of (N-2-aminoethyl-p-toluenesulfonamide) ($\eta^6$-benzene) ruthenium (II) chloride obtained in the Reference Example 3 and 9 mg (0.035 mmol) of silver triflate were prepared together with 2.5 ml (20 mmol) of methanol, 2.5 ml of isoprene and 2 ml (22 mmol) of vinyl acetate and the mixture was heated with stirring at 100° C. for 13 hours in an argon atmosphere. The reaction mixture was poured into water and the separated organic layer was analyzed by gas chromatography. As a result, the organic layer was a composition consisting of 70% of 4-methylhexa-1,5-dien-1-yl acetate, 25% of a regioisomer and 5% of a cyclic dimer of dienes.

Example 3

Synthesis of 4-methylhexa-1,5-dien-1-yl acetate 4 mg (0.016 mmol) of ($\eta^6$-benzene) ruthenium (II) dichloride, 15 mg (0.058 mmol) of silver triflate and 11.2 mg (0.052 mmol) of N-2-aminoethyl-p-toluenesulfonamide were placed in a sealed tube, which was then charged with 2 ml (20 mmol) of isoprene, 2 ml (22 mmol) of vinyl acetate and 2 ml of methanol. The mixture was heated with stirring at 100° C. for 6 hours in an argon atmosphere. The reaction mixture was poured into water and the organic layer was concentrated to obtain 0.17 g (yield: 6% based on isoprene) of a co-dimer (4-methylhexa-1,5-dien-1-yl acetate) (Purity: 75%, regioisomer: 17%, cyclic dimer of dienes: 8%).

Example 4

Synthesis of 4-methylhexa-1,5-dien-1-yl acetate 4.5 mg (0.014 mmol) of ($\eta^5$-pentamethylcyclopentadienyl) ruthenium (III) dichloride, 2 ml of methanol, 2 ml (20 mmol) of isoprene and 2 ml (22 mmol) of vinyl acetate were placed and the mixture was heated with stirring at 100° C. for 12 hours in an argon atmosphere. The reaction mixture was poured into water and the separated organic layer was analyzed by gas chromatography. As a result, the organic layer was a composition consisting of 90% of 4-methylhexa-1,5-dien-1-yl acetate, 4% of a regioisomer and 6% of a cyclic dimer of dienes.

Example 5

Synthesis of 4-methyl-1,5-hexadien-1-yl pivalate 11.8 mg (0.035 mmol) of ($\eta^5$-pentamethylcyclopentadienyl) ($\eta^4$isoprene) ruthenium (II) chloride obtained in the Reference Example 1, 1 ml (10 mmol) of isoprene, 1 ml (6.7 mmol) of vinyl pivalate and 2 ml of methanol were heated with stirring at 100° C. for 12 hours in an argon atmosphere. The reaction mixture was diluted with water and the organic layer was concentrated and distilled to yield 1.1 g (yield: 84%) of a product. No distillation residue, such as polymers, was observed and the reaction proceeded selectively (purity: 94.6%, regioisomer: 4.7%, cyclic dimer of dienes: less than 1%).

Boiling point: 110° C./10 mmHg $^1$H-NMR (200 MHz, CDCl$_3$):

$\delta$1.01(3H, d, J=6.4 Hz), 1.25(9H, s), 2.0–2.4(3H, m), 4.8–5.0(1H, m), 4.93(1H, dm, J=10.4 Hz), 4.98(1H, dm, J=17.2 Hz), 5.75(1H, ddd, J=6.8, 10.4, 17.2 Hz), 7.04(1H, dm, J=6.4 Hz)

Gas chromatography analysis:

Column: NB-1 (produced by G. L. Science)

Measurement temperature: 60–160° C. (temperature was raised at a rate of 5° C./minute)

Retention time =15.2 minutes (product), 16.2 minutes (isomer)

Example 6

Synthesis of 1-phenyl-4-methylhexa-1,5-diene 55 mg (0.16 mmol) of ($\eta^5$-pentamethylcyclopentadienyl) ($\eta^4$-isoprene) ruthenium (II) chloride obtained in the Reference Example 1, 10 ml(100 mmol) of isoprene, 10 ml (87 mmol) of styrene and 15 ml of methanol were heated with stirring at 100° C. for 12 hours in an argon atmosphere. After styrene was recovered under reduced pressure, a part of the residue was diluted with water and the organic layer was concentrated and distilled to obtain 42 mg of an objective product (purity: 89.4%, regioisomer: 7.0%, cyclic dimer of dienes: less than 1%).

Boiling point: 120° C./1 mmfg $^1$H-NMR (200 MHz, CDCl$_3$):

$\delta$1.20(3H, d, J=6.4 Hz), 2.1–2.5(3H, m), 4.9(1H, dm, J=10.6), 5.0(1H, dm, J=17.4 Hz), 5.6–5.8(1H, m), 5.7(1H, ddd, J=6.8, 10.6, 17.4 Hz), 6.5(1H, dm, J=11.8 Hz), 7.2–7.5 (5H, m)

Gas chromatography analysis:

Column: NB-1 (produced by G. L. Science)

Measurement temperature: 60–160° C. (temperature was raised at a rate of 5° C./minute)

Retention time=18.8 minutes (product), 17.4 minutes (isomer)

Example 7

Synthesis of hexa-1,5-dien-1-yl pivalate 13.6 mg (0.037 mmol) of ($\eta^5$-pentamethylcyclopentadienyl) ($\eta^4$-norbornadiene) ruthenium (II) chloride obtained in the Reference Example 2, 6 ml (74 mmol) of 1,3-butadiene, 2 ml (13.5 mmol) of vinyl pivalate and 2 ml of methanol were heated with stirring at 100° C. for 15 hours in a butadiene atmosphere. The reaction mixture was diluted with water and the organic layer was concentrated to yield 1.1 g (yield: 45%) of a product. The product was distilled to obtain 0.30 g (yield: 12%) of an addition product as a pure material.

Boiling point: 110° C./15 mmHg $^1$H-NMR (200 MHz, CDCl$_3$):

$\delta$1.25(9H, s), 2.0–2.4(4H, m), 4.8–5.1(3H, m), 5.80(1H, ddd, J=6.4, 10.2, 16.8 Hz), 7.03(1H, dt, J=6.4, 1.2 Hz)

Gas chromatography analysis:

Column: NB-1 (produced by G. L. Science)

Measurement temperature: 60–160° C. (temperature was raised at a rate of 5° C./minute)

Retention time=13.5 minutes (product)

Example 8

Synthesis of 8-methyl-4-vinyl-nona-1,7-dien-1-yl pivalate 14.6 mg (0.040 mmol) of ($\eta^5$-pentamethylcyclopentadienyl) ($\eta^4$-norbornadiene) ruthenium (II) chloride obtained in the Reference Example 2, 1.5 ml (78%, 10 mmol) of 7-methyl-3-methylene-1,6-octadiene (myrcene), 1.5 ml (10 mmol) of vinyl pivalate and 2 ml of methanol were heated with stirring at 100° C. for 15 hours in an argon atmosphere. The reaction mixture was diluted with water and the organic layer was concentrated and distilled to obtain 0.75 g (yield: 41%) of an addition product as a pure material.

Boiling point: 110° C./0.5 mmHg $^1$H-NMR (200 MHz, CDCl$_3$):

$\delta$1.25(9H, s), 1.2–1.6(2H, m), 1.58(3H, s), 1.68(3H, s), 1.9–2.4(5H, m), 4.7–5.2(4H, m), 5.60(1H, ddd, J=8.0, 11.0, 16.0 Hz), 7.03(1H, dm, J=6.4 Hz)

Gas chromatography analysis:

Column: NB-1 (produced by G. L. Science)

Measurement temperature: 60–160° C. (temperature was raised at a rate of 5° C./minute) and the temperature was raised up to 250° C. at a rate of 10° C./minute.

Retention time=25.9 minutes (product), 26.6 minutes (isomer)

Example 9

Synthesis of 8-acetoxy-8-methyl-4-vinyl-1-nonen-1-yl acetate 12.2 mg (0.033 mmol) of ($\eta^5$-pentamethylcyclopentadienyl) ($\eta^4$-norbornadiene) ruthenium (II) chloride obtained in the Reference Example 2, 1.5 g (7.6 mmol) of 2-methyl-6-methylene-7-octen-2-yl acetate (myrcenyl acetate), 2 ml (22 mmol) of vinyl acetate and 2 ml of methanol were heated with stirring at 100° C. for 15 hours in an argon atmosphere. The reaction mixture was diluted with water and the organic layer was concentrated and distilled to obtain 1.1 g (yield: 50%) of an addition product as a pure material.

Boiling point: 120° C./0.5 mmHg $^1$H-NMR (200 MHz, CDCl$_3$):

δ1.2–1.8(4H, m), 1.41(4H, s), 1.96(3H, s), 2.15(3H, s), 1.9–2.4(3H, m), 4.7–5.1(3H, m), 5.57(1H, ddd, J=8.0, 11.0, 16.2 Hz), 7.03(1H, dm, J=6.4 Hz)

Gas chromatography analysis:

Column: NB-1 (produced by G. L. Science)

Measurement temperature: 60–160° C. (temperature was raised at a rate of 5° C./minute) and the temperature was raised up to 250° C. at a rate of 10° C./minute.

Retention time=27.4 minutes (product), 27.9 minutes (isomer)

Example 10

Synthesis of 4-methylhexa-1,5-dien-1-yl acetate (p-Cymene)ruthenium dichloride dimer (27.8 mg, 0.091 mmol Ru) and sodium triflate (80 mg, 0.464 mmol) were dissolved in 10 ml of methanol. To the mixed solution were added isoprene (3 ml) and vinyl acetate (5 ml) and the mixture was stirred under heat at 100° C. for 14 hours. The resulting product was poured into water and extracted using toluene and the extract was subjected to a GLC analysis. As a result, it was confirmed that a co-dimer was produced with the conversion rate being 10% and the ratio of an isomer being 17:3.

Example 11

Synthesis of 4-methyl-1,5-hexadien-1-yl pivalate (Benzene)ruthenium dichloride dimer (14 mg, 0.056 mmol Ru), silver triflate (20 mg, 0.078 mmol) and 2,2-methylenebis(4-phenyl-2-oxazoline) (17.8 mg, 0.058 mmol) were dissolved in 2 ml of methanol. To the mixed solution were added isoprene (2 ml) and vinyl pivalate (1 ml) and the mixture was stirred under heat at 100° C. for 10 hours. The resulting product was poured into water and the separated organic layer was subjected to a GLC analysis. As a result, it was confirmed that a co-dimer was produced with the conversion rate being 72% and the ratio of an isomer being 4:1.

Example 12

Synthesis of 4-methyl-5-hexen-1-al

4-Methyl-1,5-hexadien-1-yl (8.8 g, 57 mmol) was dissolved in methanol (50 ml), to which was added 20% sulfuric acid (10 ml) and the mixture was stirred for 16 hours at room temperature. The resulting mixture was poured into an aqueous saturated sodium bicarbonate carefully and subjected to an extraction using an ether. The extract was concentrated, to which was added an aqueous acetic acid solution (acetic acid (10 ml) was mixed in water (20 ml)) and the mixed solution was stirred under heating at 100° C. for 2 hours to complete hydrolysis. The reaction mixture was poured into an aqueous sodium bicarbonate solution carefully and subjected to an extraction using an ether. The ether layer was washed with an aqueous saturated sodium bicarbonate solution, water and a saturated brine in this order once, followed by drying using sodium sulfate anhydride. The resulting substance was concentrated and distilled to obtain 4.2 g (yield: 66%) of the objective compound.

$^1$H-NMR (200 MHz, CCl$_4$): δ1.02 (3H, d, J=6 Hz), 1.10(s, 9H), 1.5(2H, m), 2.2(3H, m), 4.8–5.0(2H, m), 5.4–5.8(1H, m), 7.5(1H, t, J=4 Hz).

The resulting product is a transparent liquid which has a high diffusibility, and a strong and fresh green fruit-like fragrance.

Example 13

Preparation of an apple type blending perfume

|  | (Ratio by weight) |
|---|---|
| γ-undecalactone | 60 |
| L-citronellal | 65 |
| 1,1-dimethyl-2-phenylethyl acetate | 220 |
| Ethyl heptoate | 6 |
| Cis-3-hexen-1-ol | 25 |
| Cis-3-hexenyl acetate | 5 |
| Trans-2-hexenyl acetate | 16 |
| Hexyl acetate | 180 |
| Hydratropaldehyde (2-phenylpropanal) | 3 |
| α-ionone | 30 |
| Isoamyl butylate | 110 |
| Methyl 2-methyl butylate | 70 |
| Ethylene brassylate | 110 |
|  | 900 |

To 900 parts of the above blending perfume was added 100 parts of 4-methyl-5-hexen-1-al obtained in the Example 12 to obtain an apple type blending perfume having a fresh and green fruit-like scent. For comparison, 100 parts of cis-3-hexenal, a similar fragrant compound, was used in place of 4-methyl-5-hexen-1-al to prepare a perfume composition. The both perfumes were evaluated by five panelists in an acceptability test. As a result, five panelists all preferred the perfume containing 4-methyl-5-hexen-1-al and evaluated it as a desirable perfume composition for well-balanced shampoos which had a mild and fruity fragrance.

Example 14

Herbal green type blending perfume

|  | (Ratio by weight) |
|---|---|
| Allylamyl glycolate | 30 |
| Armoise oil | 80 |
| Basil oil | 100 |
| β-damascon | 10 |

-continued

Herbal green type blending perfume

| | (Ratio by weight) |
|---|---|
| Estragon oil | 40 |
| Galbanum oil | 30 |
| 1,3-benzodioxy-5-yl-2-methylpropanal | 150 |
| Cis-3-hexen-1-ol | 40 |
| Linalool | 370 |
| Dimethyl tetrahydrobenzaldehyde | 100 |
| | 950 |

To 950 parts of the above blending perfume was added 50 parts of 4-methyl-5-hexen-1-al obtained in the Example 12 to obtain a herbal green type blending perfume having a green smelling. For comparison, 50 parts of trans-2-hexenal, a similar fragrant compound, was used in place of 4-methyl-5-hexen-1-al to prepare a perfume composition. The both perfumes were evaluated by ten panelists in an acceptability test. As a result, nine panelists preferred the perfume containing 4-methyl-5-hexen-1-al. Their conclusion was based on the finding that the inventive composition was relatively odorless and had a mild and herbal green fragrance. They further evaluated that it was a perfume composition suitable for well-balanced men's cosmetics.

Example 15

Synthesis of 4-vinyl-8-methyl-1,7-nonadienyl acetate 30 mg (0.079 mmol) of ($\eta^5$-pentamethylcyclopentadienyl) ($\eta^4$-norbornadiene) ruthenium (II) chloride obtained in the Reference Example 2, 10 ml (78%, 46 mmol) of myrcene, 10 ml (109 mmol) of vinyl acetate and 15 ml of methanol were heated with stirring at 70° C. for 23 hours in an argon atmosphere. The reaction solution was diluted with water and the organic layer was fractionated. The organic layer was concentrated and distilled to obtain 4.8 g (yield: 47%) of the title compound (addition product) as a pure product.

Boiling point: 110° C./0.5 mmHg $^1$H-NMR (200 MHz, CDCl$_3$):

δ1.2–1.6(2H, m), 1.58(3H, s), 1.68(3H, s), 1.9–2.4(5H, m), 2.18(3H, s), 4.7–5.2(4H, m), 5.60(1H, ddd, J=8.0, 11.0, 16.0 Hz), 7.03(1H, dm, J=6.4 Hz)

Gas chromatography analysis:

Measurement temperature: 60–160° C. (temperature was raised at a rate of 5° C./minute) and then 160 to 250° C. (temperature was raised at a rate of 10° C./minute)

Retention time=23.1 minutes (23.1 minutes, 96% purity, 23.9 minutes for an isomer)

Example 16

Synthesis of 4-vinyl-8-methyl-1,7-nonadienyl pivalate 23.7 mg (0.055 mmol) of (N-2-aminomethyl-p-toluene sulfonamide) ($\eta^6$-benzene) ruthenium (II) chloride obtained in the Reference Example 4 and 17.5 mg (0.068 mmol) of silver triflate were mixed in 2 ml of methanol, to which were added 2 ml (purity: 78%, 1.25 g, 9.2 mmol) of myrcene and 1.73 g (13 mmol) of vinyl pivalate. The mixture was stirred at 70° C. for 6 hours. The reaction mixture was diluted with water and the organic layer was analyzed by gas chromatography to confirm that the title compound (addition product) having a purity of 76% (regioisomer: 26%) was produced at a conversion rate of 17%.

Example 17

Synthesis of 4-vinyl-8-methyl-7-nonenal from 4-vinyl-8-methyl-1,7-nonadienyl acetate 4.8 g (21.6 mmol) of 4-vinyl-8-methyl-1,7-nonadienyl acetate obtained in Example 16 was dissolved in 10 ml of methanol, to which was added 2 ml of 20% sulfuric acid and the mixture was stirred at room temperature for 16 hours. The resulting mixture was poured into water and the solution was subjected to an extraction using an ether. The extract was washed with an aqueous saturated sodium bicarbonate solution and with a saturated salt brine. The resulting extract was concentrated, to which aqueous acetic acid (prepared by adding 20 ml of water and 10 ml of tetrahydrofuran to 10 ml of acetic acid) was added. The mixture was heated with stirring at 100° C. for 2 hours to complete hydrolysis. The reaction mixture was poured into water and the resulting reaction mixture was subjected to an extraction using an ether. The ether layer was washed with an aqueous saturated sodium bicarbonate solution, water and a saturated salt brine in this order, followed by drying using sodium sulfate anhydride. The dried substance was concentrated and distilled to obtain 1.1 g (yield: 28%) of the title compound.

Boiling point: 120° C./5 mmHg

IR: 1726 cm$^{-1}$ (CHO)

$^1$H-NMR (200 MHz, CDCl$_3$):

δ0.8–2.1(7H, m), 1.58(3H, s), 1.66(3H, s), 2.3–2.5(2H, m), 4.8–5.2(3H, m), 5.45(1H, t, J=9.7, 11.1, 16.6 Hz), 9.78(1H, s)

The resulting product was a transparent liquid which had a high diffusibility and a strong aliphatic aldehyde-like fragrance emanating simultaneously a slightly citrus- and rose-like fragrance.

Example 18

Synthesis of 4-vinyl-8-methyl-7-nonenal from 4-vinyl-8-methyl-1,7-nonadienyl pivalate The above 4-vinyl-8-methyl-1,7-nonadienyl pivalate obtained in Example 17 instead of 4-vinyl-8-methyl-1,7-nonadienyl acetate obtained in Example 18 was hydrolyzed in the same conditions as in Example 18 to obtain the title compound, 4-vinyl-8-methyl-7-nonenal.

Example 19

| Citrus type blending perfume: | |
|---|---|
| | (Ratio by weight) |
| 1-Decanal | 7 |
| Citral | 20 |
| Citronellol 950 | 10 |
| α-damascon | 2 |
| Dihydromyrcenol | 30 |
| Ethyl 2-methyl butyrate | 1 |
| Grape fruit oil | 30 |
| Lemon oil | 160 |
| Lime oil | 200 |
| Linalool | 30 |

-continued

| Citrus type blending perfume: | |
|---|---|
| | (Ratio by weight) |
| Orange Oil | 490 |
| | 980 |

To 980 parts of the above blending perfume was added 20 parts of 4-vinyl-8-methyl-7-nonenal to obtain a citrus type blending perfume having a fresh and green smelling or feeling.

Example 20

| Green type blending perfume: | |
|---|---|
| | (Ratio by weight) |
| 1% dipropylene glycol solution of 2-trans-6-cisnonadienal | 20 |
| Benzyl salicylate | 80 |
| Cis-3-hexenol | 0.5 |
| Cyclamenaldehyl | 20 |
| Kovanol | 200 |
| L-laurynal | 40 |
| Melonal | 1.5 |
| Methyl ionone | 20 |
| Phenylethyl alcohol | 296 |
| Hexylcinnamic aldehyde | 300 |
| | 978 |

To 978 parts of the above blending perfume was added 22 parts of 4-vinyl-8-methyl-7-nonenal to obtain a melon and cucumber type blending perfume having a green smelling or feeling.

Although the invention has been described with reference to particular means, materials and embodiments, it is to be understood that the invention is not limited to the particulars disclosed and extends to all equivalents within the scope of the claims.

The present disclosure relates to subject matter contained in priority Japanese Application Nos. HEI-10-240413, HEI-10-321700, HEI-11-025781 and HEI-11-194185, filed on Aug. 26 and Nov. 12, 1998, and Feb. 3 and Jul. 8, 1999, respectively, which are herein expressly incorporated by reference in their entireties.

While the invention has been described in detail and with reference to specific embodiments thereof, it will be apparent to one skilled in the art that various changes and modifications can be made therein without departing from the spirit and scope thereof.

What is claimed is:

1. A process for producing a diene compound represented by the formula (IX):

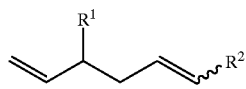

(IX)

wherein $R^1$ represents a hydrogen atom, a $C_1$–$C_6$ alkyl group which may have a substituent or a $C_2$–$C_6$ alkenyl group which may have a substituent; $R^2$ represents a phenyl group which may have a $C_1$–$C_4$ lower alkyl group, or a $C_1$–$C_{12}$ acyloxy group which may have a phenyl group, a naphthyl group or a benzyl group as a substituent, the wavy line showing a cis-isomer, a trans-isomer or mixture thereof; $R^2$ is a hydroxy group which reversibly forms an aldehyde group through shifting of the position of the double bond adjacent to said hydroxy group, said process at least comprising the step of reacting a 2-substituted-1,3-butadiene represented by the following general formula (I):

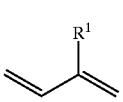

(I)

wherein $R^1$ is defined as indicated above;

with a terminal olefin represented by the following general formula (II):

(II)

wherein $R^2$ is defined as indicated above;

in a hydrophilic solvent in the presence of a ruthenium compound.

2. A process for producing a diene compound according to claim 1, wherein said $R^2$ in the formula (II) is a $C_1$–$C_{12}$ acyloxy group which may have a phenyl group, a naphthyl group or a benzyl group as a substituent.

3. A process for producing a diene compound according to claim 1, wherein said ruthenium compound comprises a ruthenium catalyst represented by the following formula (III):

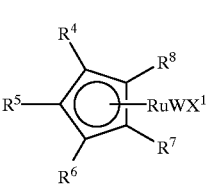

(III)

wherein $R^4$, $R^5$, $R^6$, $R^7$ and $R^8$, which may be the same or different, represent a hydrogen atom or a $C_1$–$C_4$ lower alkyl group, or two adjacent groups among $R^4$, $R^5$, $R^6$, $R^7$ and $R^8$ may be bonded to each other so as to form a five- or six-membered ring; W represents a 1,3-butadiene group, an isoprene group, a myrcene group, a 1,5-cyclooctadiene group, a norbornadiene group, a 2,3-dimethyl-1,3-butadiene group or a halogen atom; and $X^1$ represents a halogen atom.

4. A process for producing a diene compound according to claim 1, wherein said ruthenium compound comprises a ruthenium catalyst formed by mixing a ruthenium compound represented by the following formula (IV):

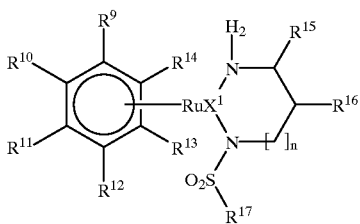

(IV)

wherein $R^9$, $R^{10}$, $R^{11}$, $R^{12}$, $R^{13}$ and $R^{14}$, which may be the same or different, represent a hydrogen atom or a $C_1$–$C_4$ lower alkyl group, or two adjacent groups among $R^9$, $R^{10}$, $R^{11}$, $R^{12}$, $R^{13}$ and $R^{14}$ may bond to each other so as to form a five- or six-membered ring; $X^1$ represents a halogen atom; $R^{15}$ and $R^{16}$ represent a hydrogen atom, a $C_1$–$C_4$ lower alkyl group, a $C_5$–$C_7$ cycloalkyl group, or a phenyl group, a naphthyl group or a benzyl group, each of which may be substituted with a $C_1$–$C_4$ lower alkyl group or with a halogen atom, or $R^{15}$ and $R^{16}$ are combined with each other to form a $C_3$–$C_6$ alkylene group; $R^{17}$ represents a hydrogen atom, a $C_1$–$C_4$ lower alkyl group, a $C_5$–$C_7$ cycloalkyl group, a lower alkyl halide, or a phenyl group, a naphthyl group or a benzyl group, each of which may be substituted with a $C_1$–$C_4$ lower alkyl group or with a halogen atom; and n denotes 0 or 1;

with salts represented by the following formula (V):

(V)

wherein M represents a mono-, di-, or tri-cation; $X^2$ represents an anion; a denotes 1 when M is a mono-cation, 2 when M is a di-cation or 3 when M is a tri-cation.

5. A process for producing a diene compound according to claim 1, wherein said ruthenium compound comprises a ruthenium catalyst formed by mixing a ruthenium compound represented by the following formula (VI):

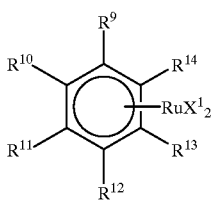

(VI)

wherein $R^9$, $R^{10}$, $R^{11}$, $R^{12}$, $R^{13}$, and $R^{14}$, which may be the same or different, represent a hydrogen atom or a $C_1$–$C_4$ lower alkyl group, or two adjacent groups among $R^9$, $R^{10}$, $R^{11}$, $R^{12}$, $R^{13}$, and $R^{14}$ may bond to each other so as to form a five- or six-membered ring, and $X^1$ represents a halogen atom;

with a salt represented by the following formula(V):

(V)

wherein M represents a mono-, di-, or tri-cation, $X^2$ represents an anion, and a denotes 1 when M is a mono-cation, 2 when M is a di-cation, or 3 when M is a tri-cation.

6. A process for producing a diene compound according to claim 1, wherein the process comprises adding a nitrogen bidentate ligand represented by the following formula (VII):

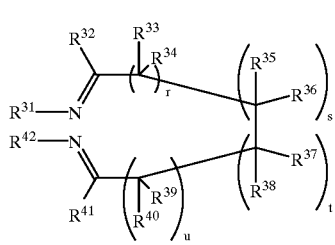

(VII)

wherein $R^{31}$ and $R^{42}$, which may be the same or different, represent an aryl group which may have a $C_1$–$C_4$ lower alkyl group, a $C_1$–$C_4$ lower alkyl group, an aralkyl group or a $C_2$–$C_4$ lower alkenyl group as a substituent; $R^{32}$ and $R^{41}$, which may be the same or different, represent an aryl group which may have a $C_1$–$C_4$ lower alkyl group, a $C_1$–$C_4$ lower alkyloxy group which may have a substituent or a hydrogen atom; $R^{31}$ and $R^{32}$ or $R^{41}$ and $R^{42}$ may form a ring which may include an oxygen atom; r, s, t and u respectively denote 0 or 1; and $R^{33}$ to $R^{40}$, which may be the same or different, respectively represent a hydrogen atom, a $C_1$–$C_4$ lower alkyl group or a $C_2$–$C_4$ lower alkenyl group, or any two groups among $R^{33}$ to $R^{40}$ may be bonded to each other so as to form a five- or six-membered ring which may have one or more substituents;

to said ruthenium catalyst so that the activity of said ruthenium catalyst is controlled.

7. A process for producing a diene compound according to claim 1, wherein said hydrophilic solvent comprises at least one solvent selected from the group consisting of methanol, ethanol, a mixture of methanol and water and a mixture of ethanol and water.

8. A process for producing a diene compound according to claim 1, wherein said 2-substituted-1,3-butadiene is at least one compound selected from the group consisting of a) isoprene b) butadiene; and c) myrcene represented by the formula (VIII):

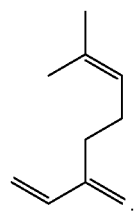

(VIII)

9. A process for producing 4-methyl-5-hexen-1-al represented by the formula (X):

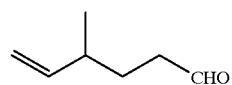

(X)

said process comprising the steps of:

a) preparing a diene compound represented by the formula (IX):

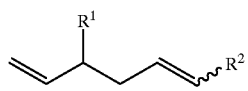

(IX)

wherein R¹ represents a methyl group; R² represents a C₁–C₁₂ acyloxy group which may have a phenyl group, a naphthyl group or a benzyl group as a substituent, R² is a hydroxy group which reversibly forms an aldehyde group through shifting of the position of the double bond adjacent said hydroxy group; and the wavy line shows a cis-isomer, a trans-isomer, or a mixture thereof;

by reacting 2-substituted-1,3-butadiene represented by the following formula (I):

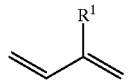

(I)

wherein R¹ represents a methyl group;

with a terminal olefin represented by the following formula (II):

(II)

wherein R² represents a C₁–C₁₂ acyloxy group which may have a phenyl group, a naphthyl group or a benzyl group as a substituent;

in a hydrophilic solvent in the presence of a ruthenium compound, to obtain a corresponding diene compound; and b) hydrolyzing said diene compound.

10. A process for producing 4-vinyl-8-methyl-7-nonenal represented by the formula (XI):

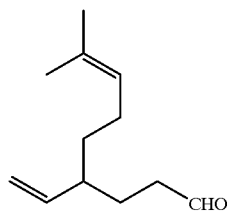

(XI)

said process comprising the steps of:

a) reacting myrcene represented by the formula (VIII):

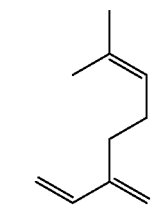

(VIII)

with a vinyl acylate represented by the following formula (XII):

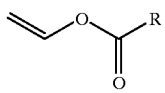

(XII)

wherein R represents a hydrogen atom, a C₁–C₄ lower alkyl group, a phenyl group, a naphthyl group or a benzyl group, each of which may have a C₁–C₄ lower alkyl group as a substituent;

in a hydrophilic solvent in the presence of a ruthenium compound, so as to form a 4-vinyl-8-methyl-1,7-nonadienyl acylate represented by the following formula (XIII):

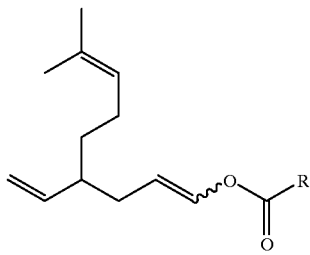

(XIII)

wherein R represents a hydrogen atom, a C₁–C₄ lower alkyl group, a phenyl group, a naphthyl group or a benzyl group, each of which may have a C₁–C₄ lower alkyl group as a substituent; and b) hydrolyzing said 4-vinyl-8-methyl-1,7-nonadienyl acylate.

11. A process for producing 4-vinyl-8-methyl-7-nonenal (XI) according to claim 10, wherein said ruthenium compound comprises a ruthenium catalyst represented by the following formula (III):

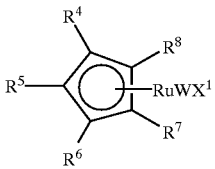

(III)

wherein $R^4$, $R^5$, $R^6$, $R^7$ and $R^8$, which may be the same or different, represent a hydrogen atom or a $C_1$–$C_4$ lower alkyl group, and two adjacent groups among $R^4$, $R^5$, $R^6$, $R^7$ and $R^8$ may be bonded to each other so as to form a five- or six-membered ring; W represents a 1,3-butadiene group, an isoprene group, a myrcene group, a 1,5-cyclooctadiene group, a norbornadiene group, a 2,3-dimethyl-1,3-butadiene or a halogen atom; and $X^1$ represents a halogen atom.

12. A process for producing 4-vinyl-8-methyl-7-nonenal according to claim 10, wherein said ruthenium compound comprises a ruthenium catalyst formed by mixing a ruthenium compound represented by the following formula (IV):

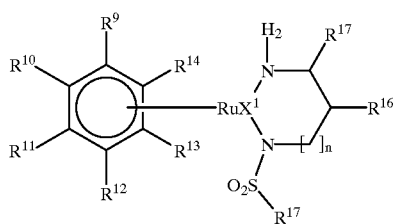

(IV)

wherein $R^9$, $R^{10}$, $R^{11}$, $R^{12}$, $R^{13}$ and $R^{14}$, which may be the same or different, represent a hydrogen atom or a $C_1$–$C_4$ lower alkyl group, or two adjacent groups among $R^9$, $R^{10}$, $R^{11}$, $R^{12}$, $R^{13}$ and $R^{14}$ may be bonded to each other so as to form a five- or six-membered ring; $X^1$ represents a halogen atom; $R^{15}$ and $R^{16}$ represent a hydrogen atom, a $C_1$–$C_4$ lower alkyl group, a $C_5$–$C_7$ cycloalkyl group, a phenyl group, a naphthyl group or a benzyl group, each of which may be substituted with a $C_1$–$C_4$ lower alkyl group or with a halogen atom, or $R^{15}$ and $R^{16}$ are combined with each other so as to form a $C_3$–$C_6$ alkylene group; $R^{17}$ represents a hydrogen atom, a $C_1$–$C_4$ lower alkyl group, a $C_5$–$C_7$ cycloalkyl group, a lower alkyl halide group, a phenyl group, a naphthyl group or a benzyl group, each of which may be substituted with a $C_1$–$C_4$ lower alkyl group or halogen atom; and n denotes 0 or 1;

with a salt represented by the following formula (V):

$$M(X^2)_a \quad \quad (V)$$

wherein M represents a mono-, di- or tri-cation; $X^2$ represents an anion; a denotes 1 when M is a mono-cation, 2 when M is a di-cation or 3 when M is a tri-cation.

13. A process for producing 4-vinyl-8-methyl-7-nonenal according to claim 10, wherein said ruthenium compound comprises a ruthenium catalyst formed by mixing a ruthenium compound represented by the following formula (VI):

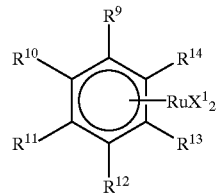

(VI)

wherein $R^9$, $R^{10}$, $R^{11}$, $R^{12}$, $R^{13}$, and $R^{14}$, which may be the same or different, represent a hydrogen atom or a $C_1$–$C_4$ lower alkyl group, or two adjacent groups among $R^9$, $R^{10}$, $R^{11}$, $R^{12}$, $R^{13}$, and $R^{14}$ may bond to each other so as to form a five- or six-membered ring, and $X^1$ represents a halogen atom;

with a salt represented by the following formula (V):

$$M(X^2)_a \quad \quad (V)$$

wherein M represents a mono-, di-, or tri-cation, $X^2$ represents an anion, and a denotes 1 when M is a mono-cation, 2 when M is a di-cation, or 3 when M is a tri-cation.

14. A process for producing 4-vinyl-8-methyl-7-nonenal according to claim 13, wherein the process comprises adding a nitrogen bidentate ligand represented by the following formula (VII):

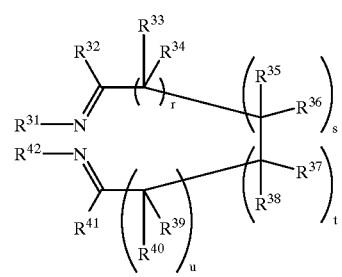

(VII)

wherein $R^{31}$ and $R^{42}$, which may be the same or different, represent an aryl group which may have a $C_1$–$C_4$ lower alkyl group, a $C_1$–$C_4$ lower alkyl group, an aralkyl group or a $C_2$–$C_4$ lower alkenyl group as a substituent; $R^{32}$ and $R^{41}$, which may be the same or different, represent an aryl group which may have a $C_1$–$C_4$ lower alkyl group as a substituent, a $C_1$–$C_4$ lower alkyloxy group which may have a substituent or a hydrogen atom; $R^{31}$ and $R^{32}$ or $R^{41}$ and $R^{42}$ may form a ring which may include an oxygen atom; r, s, t and u respectively denote 0 or 1; and $R^{33}$ to $R^{40}$, which may be the same or different, represent a hydrogen atom, a $C_1$–$C_4$ lower alkyl group or a $C_2$–$C_4$ lower alkenyl group, or any two groups among $R^{33}$ to $R^{40}$ may be bonded to each other so as to form a five- or six-membered ring which may have substituents;

to said ruthenium catalyst so that the activity of said ruthenium catalyst is controlled.

\* \* \* \* \*